United States Patent [19]

Scartazzini et al.

[11] 3,989,695

[45] Nov. 2, 1976

[54] 7β-AMINO-CEPHAM-3-OL-4-CARBOXYLIC ACID COMPOUNDS

[75] Inventors: Riccardo Scartazzini, Allschwil; Hans Bickel, Binningen, both of Switzerland

[73] Assignee: Ciba-Geigy Corporation, Ardsley, N.Y.

[22] Filed: June 26, 1973

[21] Appl. No.: 373,817

[30] Foreign Application Priority Data

June 29, 1972 Switzerland.......................... 9789/72

[52] U.S. Cl............................. 260/243 C; 424/246
[51] Int. Cl.².............. C07D 501/18; C07D 501/16; C07D 501/20
[58] Field of Search................................ 260/243 C

[56] References Cited
UNITED STATES PATENTS 3,665,003    5/1972    Kennedy et al. ................. 260/243 C
3,668,201    6/1972    Gutowski ......................... 260/243 C
3,668,202    6/1972    Foster et al. ..................... 260/243 C
3,846,416    11/1974   Kennedy et al. ................. 260/243 C

*Primary Examiner*—Nicholas S. Rizzo
*Assistant Examiner*—David E. Wheeler
*Attorney, Agent, or Firm*—Joseph G. Kolodny; John J. Maitner; Theodore O. Groeger

[57] ABSTRACT

The invention concerns 7β-amino-cepham-3-ol-4-carboxylic acid compounds, particularly esters thereof, and the N-substituted, especially N-acylated derivatives of such compounds, as well as the 3-O-esters of these compounds. They can be used as intermediates, for example, for the manufacture of the corresponding 3-unsubstituted 7β-amino-3-cephem-4-carboxylic acid compounds, which show outstanding pharmacological effects.

7 Claims, No Drawings

7β-AMINO-CEPHAM-3-OL-4-CARBOXYLIC ACID COMPOUNDS

The present invention relates to hydroxy-compounds, especially 7β-amino-cephem-3-ol-4-carboxylic acid compounds of the formula

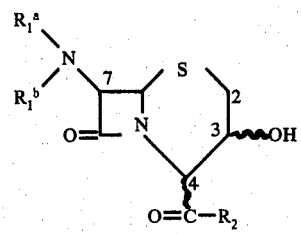

wherein $R_1^a$ represents hydrogen or an amino protective group $R_1^A$, and $R_1^b$ represents hydrogen or an acyl group Ac, or $R_1^a$ and $R_1^b$ together represent a bivalent amino protective group, and $R_2$ represents hydroxyl or a radical which together with the carbonyl grouping —C(=O)— forms a protected carboxyl group, or 3-O-esters thereof, as well as 1-oxides of compounds of the formula I, or salts of such compounds having salt-forming groups, as well as processes for their manufacture.

In the present cephem-3-ol compounds and the corresponding 1-oxides, the optionally esterified 3-hydroxyl group can have the α- or β-configuration; the compounds can be obtained in the form of mixtures of the 3-isomers or usually in the form of single 3-isomers. The carboxyl group of the formula —C(=O)—$R_2$ preferably has the α-configuration.

An amino protective group $R_1^A$ is a group which can be replaced by hydrogen, above all an acyl group Ac, also a triarylmethyl group, especially the trityl group, as well as an organic silyl group, and an organic stannyl group. A group Ac, above all represents the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclicaliphatic carboxylic acid (including formic acid) and the acyl radical of a carbonic acid half-derivative.

A bivalent amino protective group formed by the radicals $R_1^a$ and $R_1^b$ together is, in particular, the bivalent acyl radical of an organic dicarboxylic acid, preferably with up to 18 carbon atoms, above all the diacyl radical of an aliphatic or aromatic dicarboxylic acid, and also the acyl radical of an α-aminoacetic acid which is preferably substituted in the α-position and contains, for example, an aromatic or heterocyclic radical, and wherein the amino group is bonded to the nitrogen atom via a methylene radical which is preferably substituted and, for example, contains two lower alkyl groups, such as methyl groups. The radicals $R_1^a$ and $R_1^b$ can together also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—$R_2^A$ is above all an esterified carboxyl group but can also represent an anhydride group, usually a mixed anhydride group, or an optionally substituted carbamoyl or hydrazino-carbonyl group.

The group $R_2^A$ can be a hydroxyl group etherified by an organic radical, wherein the organic radical preferably contains 18 carbon atoms, which together with the —C(=O)— grouping forms an esterified carboxyl group. Examples of such organic radicals are aliphatic, cycloaliphatic, cycloaliphatic-aliphatic, aromatic or araliphatic radicals, especially optionally substituted hydrocarbon radicals of this nature, as well as heterocyclic or heterocyclic-aliphatic radicals.

The group $R_2^A$ can also denote an organic silyloxy radical as well as a hydroxyl group etherified by an organometallic radical, such as an appropriate organic stannyloxy group, especially a silyloxy or stannyloxy group which is substituted by 1 to 3, optionally substituted hydrocarbon radicals, preferably with up to 18 carbon atoms, such as aliphatic hydrocarbon radicals, and optionally by halogen, such as chlorine.

A radical $R_2^A$ which forms, with a —C(=O)— grouping, an anhydride group, above all a mixed anhydride group, is in particular an acyloxy radical, wherein acyl represents the corresponding radical of an organic carboxylic acid, preferably with 18 carbon atoms, such as of an aliphatic, cycloaliphatic, cycoaliphatic-aliphatic, aromatic or araliphatic carboxylic acid or of a carbonic acid half-derivative, such as of a carbonic acid half-ester.

A radical $R_2^A$ which forms a carbamoyl group with a —C(=O)— grouping is an optionally substituted amino group wherein substituents represent optionally substituted monovalent or bivalent hydrocarbon radicals, preferably with up to 18 carbon atoms, such as optionally substituted monovalent or bivalent aliphatic, cycloaliphatic, cycloaliphatic-aliphatic, aromatic or araliphatic hydrocarbon radicals with up to 18 carbon atoms, also appropriate heterocyclic or heterocyclic-aliphatic radicals with up to 18 carbon atoms and/or functional groups, such as optionally functionally modified, but especially free, hydroxyl and also etherified or esterified hydroxyl, wherein the etherifying or esterifying radicals have, for example, the abovementioned meanings and preferably contain up to 18 carbon atoms, as well as acyl radicals, preferably with up to 18 carbon atoms.

In a substituted hydrazinocarbonyl group of the formula —C(=O)—$R_2^A$, one or both nitrogen atoms can be substituted, possible substituents being above all optionally substituted monovalent or bivalent hydrocarbon radicals, preferably with up to 18 carbon atoms, such as optionally substituted, monovalent or bivalent aliphatic, cycloaliphatic, cycloaliphatic-aliphatic, aromatic or araliphatic hydrocarbon radicals with up to 18 carbon atoms and also appropriate heterocyclic or heterocyclic-aliphatic radicals with up to 18 carbon atoms and/or functional groups, such as acyl radicals, preferably with up to 18 carbon atoms.

O-Esters of 3-hydroxy-cepham compounds of the formula I are esters with inorganic acids, such as strong mineral acids, for example hydrogen halide acids, such as hydrochloric acid, hydrobromic acid or hydriodic acid, or organic carboxylic acids or sulphonic acids, including formic acid, such as appropriate aliphatic, cycloaliphatic, cycloaliphatic-aliphatic, aromatic, araliphatic, heterocyclic or heterocyclic-aliphatic acids, and also with carbonic acid half-derivatives.

The general concepts used in the preceding and following description have, for example, the following meanings:

An aliphatic radical, including the aliphatic radical of an appropriate carboxylic acid or sulphonic acid, as well as an appropriate ylidene radical, is an optionally substituted monovalent or divalent aliphatic hydrocarbon radical, especially lower alkyl, as well as lower alkenyl or lower alkinyl, and also lower alkylidene which can contain, for example, up to 7, preferably up to 4, carbon atoms. Such radicals can optionally be monosubstituted, disubstituted or polysubstituted by functional groups, for example by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio or phenyl-lower alkylthio, optionally substituted lower alkoxycarbonyloxy or lower alkanoyloxy, or halogen, also by oxo, nitro, optionally substituted amino, for example lower alkylamino, di-lower alkylamino, lower alkyleneamino, oxa-lower alkyleneamino or aza-lower alkyleneamino, as well as acylamino, such as lower alkanoylamino, optionally substituted carbamoylamino, ureidocarbonylamino or guanidinocarbonylamino, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl and also optionally substituted ureidocarbonyl or guanidinocarbonyl, or nitrile, optionally functionally modified sulpho, such as sulphamoyl or sulpho present in the form of a salt, or optionally O-monosubstituted or O,O-disubstituted phosphono, wherein substituents represent, for example, optionally substituted lower alkyl, phenyl or phenyl-lower alkyl, it also being possible for O-unsubstituted or O-monosubstituted phosphono to be in the form of a salt, such as in the form of an alkali metal salt.

A bivalent aliphatic radical, including the appropriate radical of a bivalent aliphatic carboxylic acid, is, for example, lower alkylene or lower alkenylene, which can optionally be monosubstituted, disubstituted or polysubstituted, for example like an aliphatic radical indicated above, and/or be interrupted by heteroatoms, such as oxygen, nitrogen or sulphur.

A cycloaliphatic or cycloaliphatic-aliphatic radical, including the cycloaliphatic or cycloaliphatic-aliphatic radical in an appropriate carboxylic acid or sulphonic acid or an appropriate cycloaliphatic or cycloaliphatic-aliphatic ylidene radical, is an optionally substituted, monovalent or bivalent, cycloaliphatic or cycloaliphatic-aliphatic hydrocarbon radical, for example monocyclic, bicyclic or polycyclic cycloalkyl or cycloalkenyl, and also cycloalkylidene, or cycloallkyl— or cycloalkenyl-lower alkyl or -lower alkenyl, as well as cycloalkyl-lower alkylidene or cycloalkenyl-lower alkylidene, wherein cycloalkyl and cycloalkylidene contains, for example, up to 12, such as 3-8, preferably 3-6, ring carbon atoms, whilst cycloalkenyl contains, for example, up to 12, such as 3-8, for example 5-8, preferably 5 or 6, ring carbon atoms and 1 to 2 double bonds, and the aliphatic part of a cycloaliphatic-aliphatic radical can contain, for example, up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the abovementioned optionally substituted lower alkyl groups or, for example, like the abovementioned aliphatic hydrocarbon radicals, by functional groups.

An aromatic radical, including the aromatic radical of an appropriate carboxylic acid or sulphonic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

A divalent aromatic radical, for example of an aromatic carboxylic acid, is above all 1,2-arylene, especially 1,2-phenylene, which can optionally be monosubstituted, disubstituted or polysubstituted, for example like the abovementioned aliphatic and cycloaliphatic hydrocarbon radicals.

An araliphatic radical, including the araliphatic radical in an appropriate carboxylic acid or sulphonic acid and also an araliphatic ylidene radical, is, for example, an optionally substituted hydrocarbon radical, such as an aliphatic hydrocarbon radical which is optionally substituted and possesses, for example, up to three optionally substituted monocyclic, bicyclic or polycyclic aromatic hydrocarbon radicals, and above all represents phenyl-lower alkyl or phenyl-lower alkenyl as well as phenyl-lower alkinyl and also phenyl-lower alkylidene, it being possible for such radicals to contain, for example, 1-3 phenyl groups and to be optionally monosubstituted, disubstituted or polysubstituted in the aromatic and/or aliphatic part, for example like the abovementioned aliphatic and cycloaliphatic radicals.

Heterocyclic groups, including those in heterocyclic-aliphatic radicals, including heterocyclic or heterocyclic-aliphatic groups in appropriate carboxylic acids or sulphonic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also appropriate partially or wholly saturated radicals and these heterocyclic radicals can optionally be monosubstituted, disubstituted or polysubstituted, for example like the abovementioned cycloaliphatic radicals. The aliphatic part in heterocyclic-aliphatic radicals has, for example, the meaning indiated for the corresponding cycloaliphatic-aliphatic or araliphatic radicals.

The acyl radical of a carbonic acid half-derivative is preferably the acyl radical of an appropriate half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester of carbonic acid which is optionally substituted, for example in the α- or β-position, as well as of a lower alkenyl, cycloalkyl, phenyl or phenyl-lower alkyl half-ester of carbonic acid which is optionally substituted in the organic radical. Acyl radicals of a carbonic acid half-ester are furthermore appropriate radicals of lower alkyl half-esters of carbonic acid, in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

An etherified hydroxyl group is above all optionally substituted lower alkoxy, wherein substituents above all represent free or functionally modified, such as etherified or esterified, hydroxyl groups, especially lower alkoxy or halogen, also lower alkenyloxy, cycloalkyloxy or optionally substituted phenyloxy, as well as heterocyclyloxy or heterocyclyl-lower alkoxy especially also optionally substituted phenyl-lower alkoxy.

An optionally substituted amino group is, for example, amino, lower alkylamino, di-lower alkylamino, lower alkyleneamino, oxa-lower alkyleneamino, thia-lower alkyleneamino, aza-lower alkyleneamino, hydroxyamino, lower alkoxyamino, lower alkanoyloxyamino, lower alkoxycarbonylamino or lower alkanoylamino.

An optionally substituted hydrazino group is, for example, hydrazino, 2-lower alkylhydrazino, 2,2-di-lower alkylhydrazino, 2-lower alkoxycarbonylhydrazino or 2-lower alkanoylhydrazino.

Lower alkyl is, for example, methyl, ethyl, n-propyl, isopropyl, n-butyl, isobutyl, sec.-butyl or tert.-butyl, as well as n-pentyl, isopentyl, n-hexyl, isohexyl or n-heptyl, wilst lower alkenyl can, for example, be vinyl, allyl, isopropenyl, 2- or 3-methallyl or 3-butenyl, lower alkinyl can, for example, be propargyl or 2-butinyl and lower alkylidene can, for example, be isopropylidene or isobutylidene.

Lower allkylene is, for example, 1,2-ethylene, 1,2- or 1,3-propylene, 1,4-butylene, 1,5-pentylene or 1,6-hexylene, whilst lower alkenylene is, for example, 1,2-ethenylene or 2-buten-1,4-ylene. Lower alkylene interrupted by hetero-atoms is, for example, oxa-lower alkylene, such as 3-oxa-1,5-pentylene, thia-lower alkylene, such as 3-thia-1,5-pentylene, or aza-lower alkylene, such as 3-lower alkyl-3-aza-1,5-pentylene, for example 3-methyl-3-aza-1,5-pentylene.

Cycloalkyl is, for example, cyclopropyl, cyclobutyl, cyclopentyl, cyclohexyl or cycloheptyl as well as adamantyl, whilst cycloalkenyl is, for example, cyclopropenyl, 1-, 2- or 3-cyclopentenyl, 1-, 2- or 3-cyclohexenyl, 3-cycloheptenyl or 1,4-cyclohexadienyl and cycloalkylidene is, for example, cyclopentylidene or cyclohexylidene. Cycloalkyl-lower alkyl or -lower alkenyl is, for example, cyclopropyl-, cyclopentyl-, cyclohexyl- or cycloheptyl-methyl, -1,1- or -1,2-ethyl, -1,1-, -1,2- or -1,3-propyl, -vinyl or -allyl, whilst cycloalkenyl-lower alkyl or -lower alkenyl represents, for example, 1-, 2- or 3-cyclopentenyl-, 1-, 2- or 3-cyclohexenyl- or 1-, 2- or 3-cycloheptenyl-methyl, -1,1- or 1,2-ethyl, -1,1-, -1,2- or -1,3-propyl, -vinyl or -allyl. Cycloalkyl-lower alkylidene is, for example, cyclohexylmethylene, and cycloalkenyl-lower alkylidene is, for example, 3-cyclohexenylmethylene.

Naphthyl is 1- or 2-naphthyl, whilst biphenylyl represents, for example, 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, 1- or 2-naphthylmethyl, styryl or cinnamyl and phenyl-lower alkylidene is, for example, benzylidene.

Heterocyclic radicals are above all optionally substituted heterocyclic radicals of aromatic character, for example appropriate monocylic, monoazacyclic, monothiacyclic or monooxacyclic radicals, such as pyrryl, for example 2-pyrryl or 3-pyrryl, pyridyl, for example 2-, 3- or 4-pyridyl and also pyridinium, thienyl, for example 2- or 3-thienyl, or furyl, for example 2-furyl, bicyclic monoazacylic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, thiazacylic, thiadiazacyclic or oxazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3-isothiazolyl, or 1,2,4- or 1,3,4-thiadiazolyl, for example 1,2,4-thiadiazol-3-yl or 1,3,4-thiadiazol-2-yl, or bicyclic diazacyclic, thiazacyclic or oxazacyclic radicals, such as benzimidazolyl, for example 2-benzimidazolyl, benzoxazolyl, for example 2-benzoxazolyl, or benzthiazolyl, for example 2-benzthiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperdyl. Heterocyclic-aliphatic radicals are lower alkyl or lower alkenyl containing heterocyclic groups, especially those mentioned above. The abovementioned heterocyclyl radicals can be substituted, for example by optionally substituted aliphatic hydrocarbon radicals, especially lower alkyl, such as methyl, or, for example like the aliphatic hydrocarbon radicals, by functional groups.

Lower alkoxy is, for example, methoxy, ethoxy, n-propoxy, isopropoxy, n-butoxy, isobutoxy sec.-butoxy, tert.-butoxy, n-pentoxy or tert.-pentoxy. These groups can be substituted, for example as in halogen-lower alkoxy, especially 2-halogen-lower alkoxy, for example 2,2,2-trichloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentyloxy, cyclohexyloxy or adamantyloxy, phenyl-lower alkoxy is, for example, benzyloxy, 1- or 2-phenylethoxy, diphenylmethoxy or 4,4'-dimethoxydiphenylmethoxy and heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio, and phenyl-lower alkylthio is, for example, benzylthio, whilst mercapto groups etherified by heterocyclyl radicals or heterocyclyl-aliphatic radicals are especially imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkanoyloxy, for example acetoxy or propionyloxy, lower alkoxycarbonyloxy, for example methoxycarbonyloxy, ethoxycarbonyloxy or tert.-butoxycarbonyloxy, 2-halogeno-lower alkoxycarbonyloxy, for example 2,2,2-trichloroethoxycarbonyloxy, 2-bromoethoxycarbonyloxy or 2-iodoethoxycarbonyloxy, or phenylcarbonylmethoxycarbonyloxy, for example phenacyloxycarbonyloxy.

Lower alkoxycarbonyl is, for example, methoxycarbonyl, ethoxycarbonyl, n-propoxycarbonyl, isopropoxycarbonyl, tert.-butoxycarbonyl or tert.-pentoxycarbonyl.

N-Lower alkyl- or N,N-di-lower alkyl-carbamoyl is, for example, N-methylcarbamoyl, N-ethylcarbamoyl, N,N-dimethylcarbamoyl or N,N-diethylcarbamoyl, whilst N-lower alkylsulphamoyl represents, for example, N-methylsulphamoyl or N,N-dimethylsulphamoyl.

A carboxyl or sulpho present in the form of an alkali metal salt is, for example, a carboxyl or sulpho present in the form of a sodium or potassium salt.

Lower alkylamino or di-lower alkylamino, is, for example, methylamino, ethylamino, dimethylamino or diethylamino, lower alkyleneamino is, for example, pyrrolidino or piperidino, oxa-lower alkyleneamino is, for example, morpholino, thia-lower alkylenamino is, for example, thiomorpholino, and aza-lower alkyleneamino is, for example piperazino or 4-methylpiperazino. Acylamino in particular represents carbamoylamino, lower alkylcarbamoylamino, such as methylcarbamoylamino, ureidocarbonylamino, guanidinocarbonylamino, lower alkoxycarbonylamino, for example methoxycarbonylamino, ethoxycarbonylamino or tert.-butoxycarbonylamino, lower alkanoylamino, such as acetylamino or propionylamino, and also phthalimido, or sulphoamino optionally present in the form of a salt, such as in the form of an alkali metal salt, for example in the form of a sodium salt or ammonium salt.

Lower alkanoyl is, for example, formyl, acetyl or propionyl.

O-Lower alkyl-phosphono is, for example, O-methyl- or O-ethyl-phosphono, O,O-di-lower alkyl-phosphono is, for example, O,O-dimethyl-phosphono or O,O-diethylphosphono, O-phenyl-lower alkyl-phosphono is, for example, O-benzyl-phosphono, and O-lower alkyl-O-phenyl-phosphono is, for example, O-benzyl-O-methyl-phosphono.

Lower alkenyloxycarbonyl is, for example, vinyloxycarbonyl, whilst cycloalkoxycarbonyl and phenyl-lower alkoxycarbonyl represent, for example, adamantyloxycarbonyl, benzyloxycarbonyl, diphenylmethoxycarbonyl or α-4-biphenyl-α-methyl-ethoxycarbonyl. Lower alkoxycarbonyl, wherein lower alkyl contains, for example, a monocyclic, monoazacyclic, monooxacyclic or monothiacyclic group, is, for example, furyl-lower alkoxycarbonyl, such as furfuryloxycarbonyl, or thienyl-lower alkoxycarbonyl, for example 2-thenyloxycarbonyl.

2-Lower alkylhydrazino and 2,2-di-lower alkylhydrazino are, for example, 2-methylhydrazino or 2,2-dimethylhydrazino, 2-lower alkoxycarbonylhydrazino is, for example 2-methoxycarbonylhydrazino, 2-ethoxycarbonylhydrazino or 2-tert.-butoxycarbonylhydrazino and lower alkanoylhydrazino is, for example, 2-acetylhydrazino.

An acyl group Ac in particular represents an acyl radical of an organic carboxylic acid, contained in a naturally occurring or biosynthetically, semi-synthetically or totally synthetically obtainable, preferably pharmacologically active, N-acyl derivative of a 6β-amino-penam-3-carboxylic acid compound or 7β-amino-3-cephem-4-carboxylic acid compound, or represents an easily removable acyl radical, especially of a carbonic acid half-derivative.

An acyl radical Ac contained in a pharmacologically active N-acyl derivative of a 6β-amino-penam-3-carboxylic acid compound or 7β-amino-3-cephem-4-carboxylic acid compound is above all a group of the formula

wherein $n$ represents O and $R^I$ denotes hydrogen or an optionally substituted cycloaliphatic or aromatic hydrocarbon radical or an optionally substituted heterocyclic radical, preferably of aromatic character, a functionally modified, for example esterified or etherified, hydroxyl or mercapto group or an optionally substituted amino group, or wherein n represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, an optionally functionally modified, preferably etherified or esterified, hydroxyl or mercapto group, an optionally functionally modified carboxyl group, an acyl group, an optionally substituted amino group or an azido group and each of the radicals $R^{II}$ and $R^{III}$ represents hydrogen, or wherein $n$ represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably has aromatic character, $R^{II}$ denotes an optionally functionally modified, for example esterified or etherified, hydroxyl or mercapto group, an optionally substituted amino group, an optionally functionally modified carboxyl or sulpho group, an optionally O-monosubstituted or O-disubstituted phosphono group, an azdio group or a halogen atom and $R^{III}$ represents hydrogen, or wherein n represents 1, each of the radicals $R^I$ and $R^{II}$ denotes a functionally modified, preferably etherified or esterified, hydroxyl group or an optionally functionally modified carboxyl group, and $R^{III}$ represents hydrogen, or wherein $n$ represents 1, $R^I$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cycloaliphatic, cycloaliphatic-aliphatic or araliphatic hydrocarbon radical which is bonded to the carbon atom by a double bond, or wherein $n$ represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R''$ denotes an optionally substituted aliphatic, cycloaliphatic, cycloaliphatic-aliphatic, aromatic or araliphatic hydrocarbon radical and $R'''$ denotes hydrogen or an optionally substituted aliphatic, cycloaliphatic, cycloaliphatic-aliphatic, aromatic or araliphatic hydrocarbon radical.

In the abovementioned acyl groups of the formula A, for example, $n$ represents 0 and $R'$ represents hyrogen or a cycloalkyl group with 5–7 ring carbon atoms which is optionally substituted, preferably in the 1-position, by amino, or a sulphoamino group which is optionally present in the form of a salt, for example in the form of an alkali metal salt, a phenyl, naphthyl or tetrahydronaphthyl group which is optionally substituted, preferably by hydroxy, lower alkoxy, for example methoxy, and/or halogen, for example chlorine, a heterocyclic group which is optionally substituted, for example by lower alkyl, for example methyl and/or phenyl, which can in turn carry substituents, such as halogen, for example chlorine, such as a 4-isoxazolyl group, or an amino group which is preferably N-substituted, for example by an optionally substituted lower alkyl radical, such as a lower alkyl radical containing halogen, for example chlorine or $n$ represents 1, $R'$ represents a 3-amino-3-carboxy-propyl radical having an optionally protected amino group and/or carboxyl group, for example a silylated amino or acylamino group and/or silylated or esterified carboxyl group, a lower alkyl group which is optionally substituted, preferably by halogen, such as chlorine, optionally substituted phenyloxy, such as phenyloxy containing hydroxyl and/or halogen, for example chlorine, amino and/or carboxyl, a lower alkenyl group, a phenyl group which is optionally substituted, such as a phenyl group containing hydroxyl, halogen, for example chlorine, and/or optionally substituted phenoxy, such as phenoxy possessing hydroxyl and/or halogen, for example chlorine, a pyridyl, pyridinium, thienyl, 1-imidazolyl or 1-tetrazolyl group which is optionally substituted, for example by lower alkyl, such as methyl, amino or aminomethyl, an optionally substituted lower alkoxy group, for example a methoxy group, a phenyloxy group which is optionally substituted, for example by hydroxyl and/or halogen, such as chlorine, a lower alkylthio group, for example n-butylthio group, or lower alkenylthio group, for example allylthio group, a phenylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol-3-ylthio, 1,3,4-thiadiazol-2-ylthio, such as 5-methyl-1,3,4-thiadiazol-2-ylthio, or 5-tetrazolylthio, such as 1-methyl-5-tetrazolylthio group, which are optionally substituted, for example by lower alkyl, such as methyl, or represents a halogen atom, especially chlorine or bromine atom, an optionally functionally modified carboxyl group, such as lower alkoxycarbonyl, for example methoxycarbonyl or ethoxycarbonyl, nitrile or carbamoyl which is optionally N-substituted, for example by lower alkyl, such as methyl, or phenyl, or represents an optionally substituted lower alkanoyl group, for example an acetyl or propionyl group, or a benzoyl group, or an azido group, and $R''$ and $R'''$ represent hydrogen, or $n$ represents 1, $R'$ represents a phenyl or thienyl group which is optionally substituted, for example by a hydroxyl and/or halogen, for example chlorine, and also represents a 1,4-cyclohexadienyl group, as well as an isoxazolyl group, for example a 4-isoxazolyl group, $R''$ represents optionally substituted amino, such as lower alkoxycarbonylamino or 2-halogeno-lower alkoxy-carbonylamino for example tert.-butoxycarbonylamino or 2,2,2-trichloroethoxycarbonylamino, or optionally substituted carbamoylamino, such as guanidinocarbonylamino, or a sulphoamino group which is optionally present in the form of a salt, for example in the form of an alkali metal salt, an azido group, a carboxyl group which is optionally present in the form of a salt, for example in the form of an alkali metal salt, or in an esterified form, for example as a lower alkoxy-carbonyl group, for example a methoxycarbonyl group or ethoxycarbonyl group, a nitrile group, a sulpho group, an optionally functionally modified hydroxyl group, especially acyloxy, such as formyloxy, as well as lower alkoxycarbonyloxy or 2-halogeno-lower alkoxycarbonyloxy, for example tert.-butoxycarbonyloxy or 2,2,2-trichloroethoxycarbonyloxy, or optionally substituted lower alkoxy or phenyloxy, a O-lower alkyl-phosphono group or O,O-di-lower alkyl-phosphono group, for example O-methylphosphono or O,O-dimethylphosphono, or a halogen atom, for example chlorine or bromine, and $R'''$ represents hydrogen, or $n$ represents 1, $R'$ and $R''$ each represent halogen, for example bromine, or lower alkoxycarbonyl, for example methoxycarbonyl, and $R'''$ represents hydrogen, or $n$ represents 1, and each of the groups $R'$, $R''$ and $R'''$ represents lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group optionally present in the form of a salt, or an amino group which is substituted by an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as 2,2,2-trichloroethoxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl, as well as by trityl) 2,6-dimethoxybenzoyl, tetrahydronaphthoyl, 2-methoxy-naphthoyl, 2-ethoxy-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, hexanoyl, octanoyl, acrylyl, crotonyl, 3-butenoyl, 2-pentenoyl, methoxyacetyl, methylthioacetyl, butylthioacetyl, allylthioacetyl, chloroacetyl, bromoacetyl, dibromoacetyl, 3-chloropropionyl, 3-bromopropionyl, aminoacetyl or 5-amino-5-carboxy-valeryl (with an amino group which is optionally substituted, for example as indicated, such as substituted by a monoacyl or diacyl radical, for example an optionally halogenated lower alkanoyl radical, such as acetyl or dichloroacetyl, or phthaloyl, and/or with an optionally functionally modified carboxyl group, for example a carboxyl group present in the form of a salt, such as a sodium salt, or in the form of an ester, such as a lower alkyl ester, for example a methyl or ethyl ester, or an aryl-lower alkyl ester, for example diphenylmethyl ester), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethyl-acrylyl, phenylacetyl, α-bromophenylacetyl, α-azido-phenylacetyl, 3-chlorophenylacetyl, 4-aminomethylphenyl-acetyl (with an amino group which is optionally substituted, for example, as indicated), phenacylcarbonyl, phenoxyacetyl, 4-trifluoromethylphenoxyacetyl, benzyloxyacetyl, phenylthioacetyl, bromophenylthioacetyl, 2-phenoxypropionyl, α-phenoxyphenylacetyl, α-hydroxyphenylacetyl, α-methoxyphenylacetyl, α-ethoxy-phenylacetyl, α-methoxy-3,4-dichlorophenylacetyl, α-cyano-phenylacetyl, especially phenylglycyl, 4-hydroxyphenylglycyl, 3-chloro-4-hydroxyphenylglycyl, or 3,5-dichloro-4-hydroxyphenylglycyl, (it being possible in these radicals, for the amino group to be optionally substituted, for example as indicated above), α-hydroxyphenylacetyl (it being possible, in these radicals, for the hydroxyl group optionally to be protected, similarly to the amino group, for example by a suitable acyl radical, especially by formyl or by an acyl radical of a carbonic acid half-ester), or α-O-methylphosphono-phenylacetyl or α-O,O-dimethyl-phosphono-phenylacetyl, also benzylthioacetyl, benzylthiopropionyl, α-carboxyphenylacetyl (with a carboxyl group which is optionally functionally modified, for example as indicated above), 3-phenylpropionyl, 3-(3-cyanophenyl)-propionyl, 4-(3-methoxyphenyl)-butyryl, 2-pyridylacetyl, 4-aminopyridiniumacetyl (optionally with an amino group which is substituted, for example as indicated above), 2-thienylacetyl, 2-tetrahydrothienylacetyl, α-carboxy-2-thienylacetyl or α-carboxy-3-thienylacetyl (optionally with a carboxyl group which is functionally modified, for example as indicated above), α-cyano-2-thienylacetyl, α-amino-2-thienylacetyl or α-amino-3-thienylacetyl (optionally with an amino group which is substituted, for example as indicated above), α-sulphophenylacetyl (optionally with a sulpho group which is functionally modified, for example like the carboxyl group), 3-thienylacetyl, 2-furylacetyl, 1-imidazolylacetyl, 1-tetrazolylacetyl, 3-methyl-2-imidazolylthioacetyl, 1,2,4-triazol-3-ylthioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical Ac, especially of a carbonic acid half-ester, is above all an acyl radical of a half-ester of carbonic acid which can be split off by reduction, for example on treatment with a chemical reducing agent, or by treatment with acid, for example with trifluoroacetic acid, such as a lower alkoxycarbonyl radical which preferably has multiple branching in the α-position, or by acylcarbonyl, especially benzoyl, radicals, or a lower alkoxycarbonyl radical which is substituted in the β-position by halogen atoms, for example tert.-butoxycarbonyl, tert.-pentoxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position is preferably polysubstituted, for example diphenylmethoxycarbonyl or α-4-biphenylyl-α-methylethoxycarbonyl, or furyl-lower alkoxycarbonyl, above all α-furyl-lower alkoxycarbonyl, for example furfuryloxycarbonyl.

A bivalent acyl group formed by the two radicals $R_1^A$ and $R_1^b$ is, for example, the acyl radical of a lower alkanedicarboxylic acid or lower alkenedicarboxylic acid, such as succinyl, or an o-arylenedicarboxylic acid, such as phthaloyl.

A further bivalent radical formed by the groups $R_1^A$ and $R_1^b$ is, for example, a 1-oxo-3-aza-1,4-butylene radical which is substituted, especially in the 2-position and contains, for example, optionally substituted phenyl or thienyl, and is optionally monosubstituted or disubstituted by lower alkyl, such as methyl, in the 4-position, for example 4,4-dimethyl-2-phenyl-1-oxo-3-aza-1,4-butylene.

An etherified hydroxyl group $R_2^A$ forms, together with the carbonyl grouping, an esterified carboxyl group which can preferably be split easily or can be converted easily into another functionally modified carboxyl group, such as into a carbamoyl or hydrazinocarbonyl group. Such a group $R_2^A$ is, for example, lower alkoxy, such as methoxy, ethoxy, n-propoxy or isopropoxy, which, together with the carbonyl grouping, forms an esterified carboxyl group.

An etherified hydroxyl group $R_2^A$ which together with a —C(=O)— grouping forms an esterified carboxyl group which can be split particularly easily represents, for example, 2-halogeno-lower alkoxy, wherein halogen preferably has an atomic weight above 19. Such a radical forms, together with the —C(=O)— grouping, an esterified carboxyl group which can easily be split on treatment with chemical reducing agents under neutral or weakly acid conditions, for example with zinc in the presence of aqueous acetic acid, or an esterified carboxyl group which can easily be converted into such a group and is, for example, 2,2,2-trichloroethoxy or 2-iodoethoxy, also 2-chloroethoxy or 2-bromoethoxy, which can easily be converted into the latter.

An etherified hydroxyl group $R_2^A$ which together with the —C(=O)— grouping represents an esterified carboxyl group which can also be split easily on treatment with chemical reducing agents under neutral or weakly acid conditions, for example on treatment with zinc in the presence of aqueous acetic acid, and also on treatment with a suitable nucleophilic reagent, for example sodium thiophenolate, is an arylcarbonylmethoxy group, wherein aryl in particular represents an optionally substituted phenyl group, and preferably phenacyloxy.

The group $R_2^A$ can also represent an arylmethoxy group wherein aryl in particular denotes a monocyclic, preferably substituted, aromatic hydrocarbon radical. Such a radical forms, together with the —C(=O)— grouping, an esterified carboxyl group which can easily be split on irradiation, preferably with ultraviolet light, under neutral or acid conditions. An aryl radical in such an arylmethoxy group contains as substituents, in particular, lower alkoxy, for example methoxy (which in the preferred phenyl radical is above all in the 3-, 4- and/or 5-posiiton) and/or above all nitro (in the case of the preferred phenyl radical preferably in the 2-position). Such radicals are, above all 3- or 4-methoxy-benzyloxy, 3,5-dimethoxy-benzyloxy, 2-nitro-benzyloxy or 4,5-dimethoxy-2-nitro-benzyloxy.

An etherified hydroxyl group $R_2^A$ can also represent a radical which, together with the —C(=O)— grouping, forms an esterified carboxyl group which can easily be split under acid conditions, for example on treatment with trifluoroacetic acid or formic acid. Such a radical is above all a methoxy group in which methyl is polysubstituted by optionally substituted hydrocarbon radicals, especially aliphatic or aromatic hydrocarbon radicals, such as lower alkyl, for example methyl, or phenyl, or is monosubstituted by a carbocyclic aryl group possessing electron-donating substituents or by a heterocyclic group of aromatic character possessing oxygen or sulphur as a ring member, or in which methyl denotes a ring member in a polycycloaliphatic hydrocarbon radical or denotes the ring member which represents the α-position to the oxygen or sulphur atom in an oxacycloaliphatic or thiacycloaliphatic radical.

Preferred polysubstituted methoxy groups of this nature are, for example, tert.-butoxy, pentoxy, diphenylmethoxy, 4,4'-dimethoxy-diphenylmethoxy or 2-(4-biphenylyl)-2-propoxy, whilst a methoxy group which contains the abovementioned substituted aryl group or the heterocyclic group is, for example, 4-methoxybenzyloxy or 3,4-dimethoxybenzyloxy, or 2-furyloxy. A polycycloaliphatic hydrocarbon radical in which the methyl of the methoxy group represents a branched, preferably triply branched, ring member, is, for example, adamantyl, such as 1-adamantyl, and an abovementioned oxacycloaliphatic or thiacycloaliphatic radical wherein the methyl of the methoxy group is the ring member which represents the α-position to the oxygen atom or sulphur atom, denotes, for example, 2-tetrahydrofuryl, 2-tetrahydropyranyl or 2,3-dihydro-2-pyranyl or corresponding sulphur analogues.

The radical $R_2^A$ can also represent an etherified hydroxyl group which, together with the —C(=O)— grouping forms an esterified carboxyl group which can be split hydrolytically, for example under weakly basic or weakly acid conditions. Such a radical is, preferably, an etherified hydroxyl group which forms an activated ester group with the —C(=O)— grouping, such as nitrophenyloxy, for example 4-nitrophenyloxy or 2,4-dinitrophenyloxy, nitrophenyl-lower alkoxy, for example 4-nitro-benzyloxy, polyhalogenophenyloxy, for example 2,4,6-trichlorophenyloxy or 2,3,4,5,6-pentachlorophenyloxy, and also cyanomethoxy, as well as acylaminomethoxy, for example phthaliminomethoxy or succinyliminomethoxy.

The group $R_2^A$ can also represent an etherified hydroxyl group which, together with the carbonyl grouping of the formula —C(=O)—, forms an esterified carboxyl group which can be split under hydrogenolytic conditions and is, for example, α-phenyl-lower alkoxy, which is optionally substituted, such as benzyloxy, 4-methoxybenzyloxy or 4-nitrobenzyloxy.

The group $R_2^A$ can also be an etherified hydroxyl group which, together with the carbonyl grouping —C(=O)—, forms an esterified carboxyl group which can be split under physiological conditions, above all lower alkanoyloxymethoxy, for example acetoxymethoxy or pivaloylmethoxy.

A silyloxy or stannyloxy group $R_2^A$ preferably contains optionally substituted aliphatic, cycloaliphatic, aromatic or araliphatic hydrocarbon radicals, such as lower alkyl, cycloalkyl, phenyl or phenyl-lower alkyl groups, and above all represents tri-lower alkylsilyloxy, for example trimethylsilyloxy or tri-lower alkylstannyloxy, for example tri-n-butylstannyloxy.

An acyloxy radical $R_2^A$ which, together with a —C(=O)— grouping, forms a mixed anhydride group which can be split, preferably hydrolytically, contains, for example, the acyl radical of one of the abovementioned organic carboxylic acids or carbonic acid half-derivatives and is, for example, lower alkanoyloxy, for example acetoxy, or lower alkoxycarbonyloxy, for example ethoxycarbonyloxy.

A radical $R_2^A$ which, together with a —C(=O)— grouping, forms an optionally substituted carbamoyl or hydrazino-carbonyl group is, for example, amino, lower alkylamino or di-lower alkylamino, such as methylamino, ethylamino, dimethylamino or diethylamino, lower alkyleneamino, for example pyrrolidino or piperidino, oxa-lower alkyleneamino, for example morpholino, hydroxylamino, hydrazino, 2-lower alkylhydrazino or 2,2-di-lower alkylhydrazino, for example 2-methylhydrazino or 2,2-dimethylhydrazino.

O-Esters of the 3-hydroxy-cepham-4-carboxylic acid compounds of the formula I are, for example, the corresponding 3-halogen compounds, for example 3-chloro, 3-bromo or 3-iodo compounds, 3-lower alkylsulphonyloxy compounds, for example methylsulphonyloxy or ethylsulphonyloxy compounds, 3-arylsulphonyloxy compounds, for example 4-methylphenylsulphonyloxy compounds, 3-lower alkanoyloxy compounds, for example 3-acetoxy or 3-propionyloxy compounds, arylcarbonyloxy compounds, for example benzoyloxy compounds, or lower alkoxycarbonyloxy compounds, for example methoxycarbonyloxy or ethoxycarbonyloxy compounds.

Salts are, in particular, those of compounds of the formula I having an acid grouping, such as a carboxyl, sulpho or phosphono group, above all metal salts or ammonium salts, such as alkali metal salts and alkaline earth metal salts, for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzyl-ethylenediamine, and also bases of the pyridine type, for example pyridine, collidine or quinoline. Compounds of the formula I which possess a basic group can also form acid addition salts, for example with inorganic acids, such as hydrochloric acid, sulphuric acid or phosphoric acid, or with suitable organic carboxylic acids or sulphonic acids, for example trifluoroacetic acid. Compounds of the formula I having an acid group and a basic group can also be in the form of an internal salt, that is to say in the form of a zwitter-ion.

The new compounds of the present invention are valuable intermediate products which can be used for the manufacture of compounds having pharmacological properties; they can be converted into such compounds, for example as described below.

Particularly valuable cepham-3-ol compounds of the formula I are those wherein $R_1^a$ denotes hydrogen or preferably an acyl radical contained in a fermentatively obtainable (that is to say naturally occurring) or biosynthetically, semisynthetically or totally-synthetically obtainable, in particular pharmacologically active, such as highly active, N-acyl derivative of a 6β-aminopenam-3-carboxylic acid compound or 7β-amino-3- cephem-4-carboxylic acid compound or an easily removable acyl radical of a carbonic acid half-derivative, especially of a carbonic acid half-ester, $R_1^b$ represents hydrogen and $R_2$ represents hydroxyl, lower alkoxy which is optionally substituted, for example by optionally substituted aryloxy, for example 4-methoxyphenyloxy, lower alkanoyloxy, for example acetoxy or pivaloyloxy, or arylcarbonyl, for example benzoyl, or halogen, for example chlorine, bromine or iodine, such as lower alkoxy, for example methoxy, ethoxy, n-propoxy, isopropoxy, n-butoxy, tert.-butoxy or tert.-pentoxy, bis-phenyloxy-methoxy which is optionally substituted by lower alkoxy, for example bis-4-methoxyphenyloxy-methoxy or phenacyloxy, lower alkanoyloxy-methoxy, for example (acetoxy-methoxy or pivaloyloxymethoxy, or 2-halogeno-lower alkoxy, for example 2,2,2-trichloroethoxy, 2-chloroethoxy, 2-bromoethoxy or 2-iodoethoxy, or $R_2$ represents optionally substituted phenyl-lower alkoxy, especially 1-phenyl-lower alkoxy, such as phenylmethoxy, it being possible for such radicals to contain 1–3 phenyl radicals which are optionally substituted, for example by lower alkoxy, such as methoxy, nitro or phenyl, for example benzyloxy, 4-methoxy-benzyloxy, 2-biphenylyl-2-propoxy, 4-nitro-benzyloxy, diphenylmethoxy, 4,4'-dimethoxydiphenylmethoxy or trityloxy, or represents acyloxy, such as lower alkoxycarbonyloxy, for example methoxycarbonyloxy or ethoxycarbonyloxy, or lower alkanoyloxy, for example acetoxy, or represents tri-lower alkylsilyloxy, for example trimethylsilyloxy, or represents amino or hydrazino which is optionally substituted, for example by lower alkyl, such as methyl, or hydroxyl, for example amino, lower alkylamino or di-lower alkylamino, such as methylamino or dimethylamino, hydrazino, 2-lower alkylhydrazino or 2,2-di-lower alkylhydrazino, for example 2-methylhydrazino or 2,2-dimethylhydrazino or hydroxyamino, as well as the 1-oxides of these compounds, and also the 3-O-esters of such compounds with hydrogen halide acids, for example hydrochloric acid, hydrobromic acid or hydriodic acid, with lower alkanesulphonic acids, for example methanesulphonic acid, with optionally substituted phenylsulphonic acids, for example 4-methylphenylsulphonic acid, and especially with lower alkanecarboxylic acids, for example acetic acid or propionic acid, as well as with optionally substituted benzoic acids, for example benzoic acid, and also salts of such compounds having salt-forming groups.

Above all, in a cepham-3-ol compound of the formula I, and in a corresponding 1-oxide, and also in a 3O-ester of such compounds with hydrogen halide acids, for example hydrochloric acid, hydrobromic acid or hydriodic acid, with lower alkanesulphonic acids, for example methanesulphonic acid or ethanesulphonic acid, with optionally substituted phenylsulphonic acids, for example 4-methylphenylsulphonic acid, and especially with lower alkanecarboxylic acids, for example acetic acid or propionic acid, as well as with optionally substituted benzoic acids, for example benzoic acid, and in salts of such compounds which have salt-forming groups, $R_1^a$ represents hydrogen or an acyl radical contained in fermentatively obtainable (that is to say naturally occurring) or biosynthetically obtainable N-acyl derivatives of 6β-amino-penam-3-carboxylic acid compounds or 7β-amino-3-cephem-4-carboxylic acid compounds, such as a phenylacetyl or phenyloxyacetyl radical which is optionally substituted, also a lower alkanoyl or lower alkenoyl radical which is optionally substituted, for example 4-hydroxy-phenylacetyl, hexanoyl, octanoyl or n-butylthioacetyl, and especially 5-amino-5-carboxy-valeryl, wherein the amino and/or the carboxyl groups are optionally protected and are present, for example, as acylamino or esterified carboxyl, phenylacetyl or phenyloxyacetyl, or an acyl radical occurring in highly active N-acyl derivatives of 6β-amino-penam-3-carboxylic acid compounds or 7β-amino-3-cephem-4-carboxylic acid compounds, such as formyl,2-chloroethylcarbamoyl, cyanoacetyl, 2-thienylacetyl or 1-tetrazolylacetyl, especially phenylglycyl, wherein phenyl represents phenyl which is optionally substituted, for example by optionally protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxyphenyl, optionally with protected hydroxyl groups, and wherein the amino group is optionally substituted and represents, for example, a sulphoamino group optionally present in the form of a salt, or an amino group which contains, as substituents, a hydrolytically removable trityl group or an optionally substituted carbamoyl group, such as an optionally substituted ureidocarbonyl group, for example ureidocarbonyl or N'-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as 2,2,2-trichloroethoxycarbonyl, 2-chloroethoxycarbonyl, 2-bromoethoxycarbonyl, 2-iodoethoxycrbonyl, tert.-butoxycarbonyl or phenacyloxycarbonyl, or of a carbonic acid halfamide, such as carbamoyl or N-methylcarbamoyl, or wherein the amino group is bonded to the nitrogen atom of the 7β-amino group by a methylene group which optionally contains lower alkyl, such as two methyl, also thienylglycyl, such as 2-thienylglycyl (optionally with an amino group which is substituted, for example as indicated above) or 1-aminocyclohexylcarbonyl (optionally with an amino group which is substituted, for example as indicated above), also α-carboxyphenylacetyl or α-carboxy-2-thienylacetyl (optionally with a carboxyl group which is functionally modified, for example a carboxyl group which is in the form of a salt, such as a sodium salt, or in the form of an ester, such as a lower alkyl ester, for example methyl ester or ethyl ester, or phenyllower alkyl ester, for example diphenylmethyl ester) α-sulphophenylacetyl (optionally with a sulpho group which is functionally modified, for example like the carboxyl group), α-phosphono-, α-O-methylphosphono- or α-O,O-dimethyl-phosphono-phenylacetyl, or α-hydroxy-phenylacetyl (optionally with a functionally modified hydroxyl group, especially with an acyloxy group, wherein acyl denotes an acyl radical which can be split off, preferably easily, for example on treatment with an acid agent, such as trifluoroacetic acid, or with a chemical reducing agent, such as zinc in the presence of aqueous acetic acid, or denotes an acyl radical which can be converted into such an acyl radical, preferably a suitable acyl radical of a carbonic acid half-ester, such as 2,2,2-trichloroethoxycarbonyl, 2-chloroethoxycarbonyl, 2-bromoethoxycarbonyl, 2-iodoethoxycarbonyl, tert.-butoxycarbonyl or phenacyloxycarbonyl, and also formyl), for example an acyl radical of the formula A, and $R_1{}^b$ represents hydrogen, and $R_2$ represents hydroxyl, lower alkoxy, especially α-poly-branched lower alkoxy, for example tert.-butoxy, also methoxy or ethoxy, 2-halogeno-lower alkoxy, for example 2,2,2-trichloroethoxy, 2-iodoethoxy or 2-chloroethoxy or 2-bromoethoxy which can easily be converted into 2-iodoethoxy, phenacyloxy, 1-phenyl-lower alkoxy with 1-3 phenyl radicals which are optionally substituted by lower alkoxy or nitro, for example 4-methoxybenzyloxy, 4-nitrobenzyloxy, diphenylmethoxy, 4,4'-dimethoxy-diphenylmethoxy or trityloxy, lower alkanoyloxymethoxy, for example acetoxymethoxy or pivaloyloxymethoxy, lower alkoxycarbonyloxy, for example ethoxycarbonyloxy, or lower alkanoyloxy, for example acetoxy.

The invention above all relates to cephem-3-ol compounds of the formula I, wherein $R_1{}^b$ denotes hydrogen and $R_1{}^a$ denotes hydrogen or an acyl group of the formula

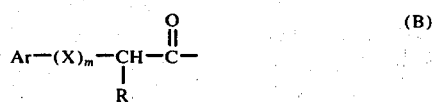

wherein Ar represents phenyl or hydroxyphenyl, for example 3- or 4-hydroxyphenyl, or hydroxy-chlorophenyl, for example 3-chloro-4-hydroxyphenyl or 3,5-dichloro-4-hydroxy-phenyl, it being possible for hydroxy substituents in such radicals to be protected by acyl radicals, such as optionally halogenated lower alkoxycarbonyl radicals, for example tert.-butoxycarbonyl or 2,2,2-trichloroethoxycarbonyl, as well as thienyl, e.g. 2- or 3-thienyl, or 1,4-cyclohexadienyl or 4-isothiazolyl, X represents oxygen or sulphur, m represents 0 or 1 and R represents hydrogen or, if m represents 0, R represents optionally protected amino, such as acylamino, for example α-polybranched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or 3-guanylureido, also sulphoamino or tritylamino, as well as optionally protected carboxyl, for example esterified carboxyl, such as phenyl-lower alkoxycarbonyl, for example diphenylmethoxycarbonyl, optionally protected sulpho, such as sulpho present in the form of an alkali metal salt, for example the form of a sodium salt, optionally protected hydroxyl, such as acyloxy, for example α-polybranched lower alkoxycarbonyloxy, such as tert.-butoxycarbonyloxy or 2-halogeno-lower alkoxycarbonyloxy, such as 2,2,2-trichloroethoxycarbonyloxy, 2-iodoethoxycarbonyloxy or 2-bromoethoxycarbonyloxy, also formyloxy, or O-lower alkylphosphono or O,O-di-lower alkylphosphono, for example O-methyl-phosphono or O,O-dimethyl-phosphono, or denotes a 5-amino-5-carboxy-valeryl radical, wherein the amino and carboxyl group are optionally protected and are, for example, present as acylamino, for example lower alkanoylamino, such as acetylamino, halogeno-lower alkanoylamino such as dichloroacetylamino, or phthaloylamino, or as esterified carboxyl, such as phenyl-lower alkoxycarbonyl, for example diphenylmethoxycarbonyl, whereby advantageously m is 1, when Ar represents phenyl, hydroxy-phenyl or hydroxy-chlorophenyl, and m is 0 and R is different from hydrogen, when Ar is phenyl, hydroxy-phenyl, hydroxy-chlorophenyl, thienyl, isothiazolyl or 1,4-cyclohexadienyl, $R_2$ denotes hydroxy, lower alkoxy, especially α-polybranched lower alkoxy, for example tert.-butoxy, 2-halogeno-lower alkoxy, for example 2,2,2-trichloroethoxy, 2-iodoethoxy or 2-bromoethoxy, or diphenylmethoxy which is optionally substituted, for example, by lower alkoxy, for example methoxy, for example diphenylmethoxy or 4,4'-dimethoxy-diphenylmethoxy, as well as the corresponding 1-oxides thereof, and the 3-O-esters of these compounds with lower alkanecarboxylic acids, for example acetic acid or propionic acid, and also the salts of such compounds having salt-forming groups.

In cepham-3-ol compounds of the formula I which are to be regarded as particularly valuable, or 3-O-esters thereof with lower alkanecarboxylic acids, for example acetic acid or propionic acid, $R_1{}^a$ represents hydrogen, the acyl radical of the formula B, wherein Ar denotes phenyl, as well as hydroxy-phenyl, e.g. 4-hydroxy-phenyl, thienyl, e.g. 2-thienyl, 4-isothiazolyl or 1,4-cyclohexadienyl, X denotes oxygen m denotes 0 or 1 and R denotes hydrogen, or, if m represents 0, denotes optionally protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally protected hydroxyl, such as acyloxy, for example α-polybranched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or represents a 5-amino-5-carboxyvaleryl radical, wherein the amino and carboxyl group are optionally protected and, for example, are in the form of acylamino, for example lower alkanoylamino, such as acetylamino, halogeno-lower alkanoylamino, such as dichloroacetylamino, or phthaloylamino, or of esterified carboxyl, such as phenyl-lower alkoxycarbonyl, for example diphenylmethoxycarbonyl, whereby advantageously m represents 1, when Ar is phenyl or hydroxy-phenyl, $R_1{}^b$ represents hydrogen, $R_2$ denotes hydroxyl and also lower alkoxy which is optionally halogen-substituted, for example chlorine-substituted, bromine-substituted or iodine-substituted, in the 2-position, especially α-polybranched lower alkoxy, for example tert.-butoxy, or 2-halogeno-lower alkoxy, for example 2,2,2-trichloroethoxy, 2-iodoethoxy or 2-bromoethoxy, or optionally lower alkoxy-substituted, such as methoxy-substituted, diphenylmethoxy, for example diphenylmethoxy or 4,4'-dimethoxy-diphenylmethoxy.

The invention above all concerns 7β-(α-$R_a$-α-$R_b$-acetylamino)-cepham-3-ol-4-carboxylic acids and the 3-O-acetyl compounds thereof and particularly the diphenylmethyl esters of such acids, wherein $R_a$ is phenyl and $R_b$ is hydrogen or optionally protected amino, such as acylamino, for example α-polybranched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino, or salts of such compounds having salt-forming groups.

The compounds of the formula I are obtained by reducing the oxo group in the 3-position in a cepham-3-one compound of the formula

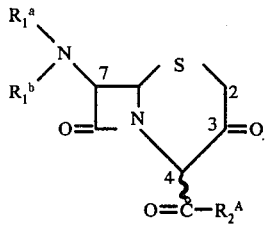

or in a 1-oxide thereof or in a mixture of a compound of the formula II and the corresponding 1-oxide and, if desired, separating a resulting mixture of a compound of the formula I and of the corresponding 1-oxide or reducing it to the compound of the formula I or oxidising it to the 1-oxide of a compound of the formula I and/or, if desired, oxidising a resulting compound of the formula I to the 1-oxide thereof or reducing a resulting 1-oxide of a compound of the formula I to the corresponding compound of the formula I and/or, if desired, in a resulting compound converting the 3-hydroxyl group into an esterified hydroxyl group and/or, if desired, in a resulting compound converting the protected carboxyl group of the formula —C(=O)—$R_2^A$ into the free carboxyl group and/or, if desired, converting a resulting compound into another compound and/or, if desired, converting a resulting compound having a salt-forming group into a salt or a resulting salt into the free compound or into another salt and/or, if desired, separating a resulting isomer mixture into the individual isomers.

A starting material of the formula II can also be employed as a mixture of a compound of the formula II and of a 1-oxide thereof. It can be in the keto form or in the enol form, in which the double bond can occupy the 2,3-position or the 3,4-position. Furthermore, the protected carboxyl group of the formula —C(=O)—$R_2^A$ in the 4-position in a keto or 2,3-enol compound preferably has the α-configuration.

In the process according to the invention, and in additional measures which may require to be carried out it is possible, if necessary, transiently to protect free functional groups, which do not participate in the reaction, in the starting substances, or in the compounds obtainable according to the process, for example free amino groups by, for example, acylation, tritylation or silylation, free hydroxyl or mercapto groups by, for example, etherification or esterification, and free carboxyl groups by, for example, esterification, including silylation in a manner which is in itself known and in each case to liberate them after the reaction has taken place, if desired, individually or conjointly, in a manner which is in itself known.

Thus, for example, in a starting material of the formula II $R_1^a$ preferably represents an amino protective group $R_1^A$, especially an acyl group Ac, wherein optionally present free functional groups, for example amino, hydroxyl, carboxyl or phosphono groups, can be protected in a manner which is in itself known, amino groups, for example, by acylation, tritylation, silylation or stannylation and hydroxyl, carboxyl or phosphono groups, for example, by etherification or esterification, including silylation or stannylation, and $R_1^b$ represents hydrogen, whereas $R_2^A$ preferably represents an etherified hydroxyl group $R_2^A$ which, with the —C(=O)— grouping, forms an esterified carboxyl group which can be split, especially split under mild conditions, it being possible for functional groups optionally present in a carboxyl protective group $R_2^A$ to be protected in a manner which is in itself known, for example as indicated above. A group $R_2^A$ is, for example, in particular an optionally halogen-substituted lower alkoxy group, such as an α-poly-branched lower alkoxy, for example tert.-butoxy, or 2-halogeno-lower alkoxy, wherein halogen represents, for example, chlorine, bromine or iodine, above all 2,2,2-trichloroethoxy, 2-bromoethoxy or 2-iodoethoxy, or an optionally substituted, such as a lower alkoxy-, for example methoxy-, or nitro-substituted 1-phenyl-lower alkoxy group, such as benzyloxy or diphenylmethoxy which is optionally substituted, for example as indicated, for example benzyloxy, 4-methoxybenzyloxy, 4-nitrobenzyloxy, diphenylmethoxy or 4,4'-dimethoxydiphenylmethoxy. The carboxyl group in the 4-position and/or the amino group in the 7-position, as well as further suitable functional groups in the radicals $R_1^A$, $R_1^b$ and/or $R_2^A$ in starting substances of the formula II, can also be protected by organic silyl or stannyl radicals, such as tri-lower alkylsilyl, for example trimethylsilyl.

The reduction of the 3-keto group in starting substances of the formula II can be carried out using suitable keto-reducing agents. Thus, it is possible to use catalytically activated hydrogen, the hydrogen being used in the presence of a hydrogenation catalyst, such as a palladium, nickel, rhodium, ruthenium or platinum catalyst, for example using hydrogen together with platinum or platinum oxide in the presence of a solvent, such as an alcohol, such as a lower alkanol, for example methanol, or ethanol, or acetic acid, and optionally under pressure.

Preferably, reduction is carried out with the aid of metallic reducing agents ("nascent hydrogen"), but above all with hydride reducing agents. Metallic reducing agents are, for example, reducing metals or reducing metal compounds, for example reducing metal alloys, amalgams or salts, such as aluminium amalgams, which is usually employed in the presence of hydrogen-releasing agents, an amalgam, for example, in the presence of an aqueous inert organic solvent, such as an ether. Hydride reducing agents are above all complex metal hydrides, preferably appropriate borohydrides, such as alkali metal borohydrides, for example sodium borohydride or lithium borohydride, also zinc borohydride, and organic alkali metal aluminium hydrides, such as tri-lower alkoxy-alkali metal aluminium hydrides, for example tri-tert.-butoxy-lithium aluminium hydride, which are usually employed in the presence of solvents, especially of relatively polar solvents, such as alcohols, for example lower alkanols, such as methanol or ethanol, or ethers, such as aliphatic ethers, for example glycol ethers and polyglycol ethers, such as ethylene glycol dimethyl ether or diethylene glycol dimethyl ether, or cyclic ethers, such as tetrahydrofurane or dioxane, or solvent mixtures, especially also aqueous solvents, the reaction being carried out at temperatures of about −20° C to about +80° C, if necessary in a closed vessel and/or in an inert gas atmosphere, for example a nitrogen atmosphere.

The above reduction of a compound of the formula II or of a 1-oxide or of a mixture of the two compounds can, depending on the type of starting material employed, lead to single compounds or mixtures. If, for example, a mixture of a starting material of the formula II and of the corresponding 1-oxide is used, it is also possible to obtain a mixture of a compound of the formula I and of the corresponding 1-oxide. Such a mixture can be separated into the individual components with the aid of the customary methods of separation, for example adsorption (such as chromatography, for example column chromatography, paper chromatography or platinum chromatography), with the aid of a suitable adsorbent, such as silica gel, cellulose or aluminium oxide, and elution, fractional crystallisation, solvent distribution (for example counter-current distribution) and the like. Furthermore, a mixture, obtainable according to the process, of a compound of the formula I and of the corresponding 1-oxide can either be directly oxidised to the 1-oxide or be reduced to the compound of the formula I; this oxidation or reduction can be carried out, for example, as described below.

A resulting compound of the formula II can be converted into the corresponding 1-oxide by treatment with a suitable oxidising agent. Suitable oxidising agents are inorganic per-acids which have a reduction potential of at least +1.5 volt and which consist of non-metallic elements, organic per-acids or mixtures of hydrogen peroxide and acids, especially organic carboxylic acids, having a dissociation constant of at least $10^{-5}$. Suitable per-acids are appropriate percarboxylic acids and persulphonic acids which can be added as such or can be formed in situ by the use of at least one equivalent of hydrogen peroxide and of a carboxylic acid. It is desirable to use a large excess of the carboxylic acid if, for example, acetic acid is used as the solvent. Suitable per-acids are, for example, performic acid, peracetic acid, trifluoroperacetic acid, permaleic acid, perbenzoic acid, 3-chloroperbenzoic acid, monoperphthalic acid or p-toluenepersulphonic acid.

The oxidation can also be carried out using hydrogen peroxide and catalytic amounts of an acid having a dissociation constant of at least $10^{-5}$, it being possible to employ low concentrations, for example 1-2% or less, but also larger amounts, of the acid. The activity of the mixture above all depends on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Acids suitable as catalysts are, for example, acetic acid, perchloric acid and trifluoroacetic acid. Usually, at least equimolar amounts of the oxidising agent, and preferably a small excess of about 10% to about 20%, are used, it also being possible to use a larger excess, that is to say up to the 10-fold amount of the oxidising agent, or above. The oxidation is carried out under mild conditions, for example at temperatures of about −50° C to about +100° C, preferably of about −10° C to about +40° C. Depending on the oxidising agent used, the 1α-oxide or 1β-oxide or a mixture of both is obtained.

A resulting 1-oxide of a compound of the formula I can be converted into the corresponding compound of the formula I by reduction. Possible reducing agents are: catalytically activated hydrogen, using noble metal catalysts which contain palladium, platinum or rhodium and which are optionally employed together with a suitable carrier, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitrilotriacetic acid; reducing dithionite, iodide or ferrocyanide anions which are used in the form of appropriate inorganic or organic salts, such as alkali metal salts, for example sodium dithionite or potassium dithionite, sodium iodide or potassium iodide, or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinous, phosphonous or phosphorous acids, as well as phosphorus-sulphur compounds corresponding to these phosphorus-oxygen compounds, in which compounds organic radicals above all represent aliphatic, aromatic or araliphatic radicals, or example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethylene-iminium salts, especially chlorides or bromides, wherein the iminium group is substituted by a bivalent or two monovalent organic radicals, such as optionally substituted lower alkylene or lower alkyl groups, such as N-chloromethylene-N,N-diethyliminium chloride or N-chloromethylene-pyrrolidiniminium chloride; and complex metal hydrides, such as sodium borohydride, in the presence of suitable activating agents, such as cobalt-II chloride, as well as borane dichloride.

As activating agents which are used together with those of the abovementioned reducing agents which do not themselves possess Lewis acid properties, that is to say which above all are employed together with the dithionite, iodide or ferrocyanide reducing agents or the trivalent phosphorus reducing agents which do not contain halogen, or in the catalytic reduction, there should especially be mentioned organic carboxylic acid halides and sulphonic acid halides, also sulphur halides, phosphorus halides or silicon halides having the same or a greater second order hydrolysis constant than benzoyl chloride, or example phosgene, oxalyl chloride, acetic acid chloride or acetic acid bromide, or chloroacetic acid chloride; pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethylchlorosilane or trichlorosilane and also suitable acid anhydrides, such as trifluroacetic acid anhydride, or cyclic sultones, such as ethanesultone, 1,3-propensultone, 1,4-butanesultone or 1,3-hexanesultone.

The reduction is preferably carried out in the presence of solvents or mixtures thereof, the choice of which is above all determined by the solubility of the starting substances and the choice of the reducing agent such as, for example, lower alkanecarboxylic acids or esters thereof, such as acetic acid and ethyl acetate, in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofurane or dioxane, ketones, for example acetone, or sulphones, especially aliphatic sulphones, or example dimethylsulphone or tetramethylenesulphone, and the like, in the case of the chemical reducing agents, these solvents preferably not containing any water. The reaction is usually carried out at temperatures of about −20° C to about 100° C, it being possible to carry out the reaction at lower temperatures if very reactive activating agents are used.

In compounds of the formula I obtainable according to the invention, or in their 1-oxides, the 3-hydroxyl group can be converted into an esterified hydroxyl group in a manner which is in itself known, it being necessary for at least $R_1^a$ in a compound of the formula I to be different from hydrogen, if the risk of simultaneous acylation of a free amino group is to be avoided. Thus, for example, a hydroxyl group esterified by a hydrogen halide acid can be formed by treatment with a suitable halogenating agent, using, for example, appropriate halogen-sulphur or halogen-phosphorus compounds, such as thionyl halides, for example thionyl chloride, or phosphorus trihalides, for example phosphorus tribromide, or quaternary halides, such as carbodiimidium halides, or example N-methyl-N,N'-dicyclohexyl-carbodiimidium iodide, if necessary in the presence of inert solvents, such as optionally halogenated, aliphatic, cycloaliphatic or aromatic hydrocarbons, for example benzene, or ethers, for example tetrahydrofurane, and, if necessary, with cooling or warming and/or in an inert gas atmosphere.

Hydroxyl groups esterified by organic sulphonic acids can preferably be formed by treatment with a reactive derivative of an organic sulphonic acid, such as an appropriate halide, fpr example chloride, if necessary in the presence of an acid-neutralising basic agent, for example an inorganic or organic base, for example analogously to the esters with carboxylic acids.

The hydroxyl group in the cepham-3-ol compounds obtainable according to the invention can also be converted into a hydroxyl group esterified by an organic carboxylic acid and into a hydroxyl group esterified by a carbonic acid half-derivative. For this, the appropriate organic carboxylic acid or a reactive acid derivative thereof is used, above all an anhydride of the carboxylic acid, such as a symmetrical anhydride, a mixed anhydride, for example a mixed anhydride with a hydrogen halide acid, that is to say a corresponding acid halide, for example acid fluoride or acid chloride, and also the anhydride with hydrocyanic acid or hydrazoic acid, that is to say the cyanocarbonyl compound or azidocarbonyl compound corresponding to the carboxylic acid, or a mixed anhydride with an organic carboxylic acid or a carbonic acid half-derivative, such as a mixed anhydride which can be formed, for example, with a halogenoformic acid lower alkyl ester, such as chloroformic acid ethyl ester or chloroformic acid isobutyl ester, or with trichloroacetic acid chloride, or an internal anhydride of a carboxylic acid, that is to say a ketene, or of carbamic acid or thiocarbamic acid, that is to say an insocyanate or isothiocyanate, or an activated ester of an acid, preferably a phenyl ester which is substituted, for example by nitro or halogen, such as chlorine, for example pentachlorophenyl, 4-nitrophenyl or 2,4-dinitrophenyl esters, hetero-aromatic esters, such as benztriazole esters, for example 2-benztriazole esters, or diacylimino esters, such as succinylimino or phthalylimino, esters. If such acylating agents are used, the reaction is carried out, if necessary, in the presence of suitable condensation agents, when using acids, for example, in the presence of carbodiimide compounds, such as dicyclohexylcarbodiimide, or carbonyl compounds, such as diimidazolylcarbonyl, and when using reactive acid derivatives, for example, in the presence of basic agents, such as tri-lower alkylamines, for example triethylamine, or heterocyclic bases, for example, pyridine. The acylation reaction can be carried out in the absence or presence of a solvent or solvent mixture, with cooling, at room temperature, or with warming and, if necessary, in a closed vessel and/or in an inert gas atmosphere, for example a nitrogen atmosphere. Suitable solvents are, for example, optionally substituted, especially optionally chlorinated, aliphatic, cycloaliphatic or aromatic hydrocarbons, such as benzene or toluene, it also being possible to use suitable esterifying reagents, such as acetic anhydride, as diluents.

The 3-hydroxy group in a cepham-3-ol compound of the formula I can also be esterified stepwise. Thus it is possible, for example, to carry out a reaction with a carbonic acid dihalide, for example phosgene, and to treat the 3-halogenocarbonyloxy compounds, such as a 3-chlorocarbonyloxy compound, thus obtainable, with an alcohol, for example a lower alkanol and thus to manufacture cepham-3-ol compounds wherein the 3-hydroxyl group is esterified by a carbonic acid half-ester.

In a compound of the formula I obtainable according to the invention and possessing a protected, especially esterified, carboxyl group of the formula —C(=O)—$R_2^A$, the latter can be converted into the free carboxyl group in a manner which is in itself known, for example depending on the nature of the group $R_2^A$. An esterified carboxyl group, for example a carboxyl group esterified by a lower alkyl radical, especially methyl or ethyl, can be converted into a free carboxyl group by hydrolysis in a weakly basic medium, for example by treatment with an aqueous solution of an alkali metal hydroxide or carbonate or alkaline earth metal hydroxide or carbonate, for example sodium hydroxide or potassium hydroxide, preferably at a pH value of up to about 9, and optionally in the presence of a lower alkanol. A carboxyl group esterified by a suitable 2-halogeno-lower alkyl group or by an arylcarbonylmethyl group can be split, for example, by treatment with a chemical reducing agent, such as a metal, for example zinc, or a reducing metal salt, such as a chromium-II salt, for example chromium-II chloride, usually in the presence of a hydrogen donor which is capable of producing nascent hydrogen together with the metal, such as an acid, above all acetic acid and also formic acid, or an alcohol, water being added preferably, a carboxyl group esterified by an arylcarbonylmethyl group can also be split by treatment with a nucleophilic, preferably salt-forming, reagent, such as sodium thiophenolate or sodium iodide, a carboxyl group esterified by a suitable arylmethyl group can be split, for example, by irradiation, preferably with ultraviolet light, for example below 290 m$\mu$, if the arylmethyl group represents, for example, a benzyl radical which is optionally substituted in the 3-, 4- and/or 5-position, for example by lower alkoxy and/or nitro groups, or with ultraviolet light of longer wavelengths, for example above 290 m$\mu$, if the arylmethyl group denotes, for example, a benzyl radical which is substituted by a nitro group in the 2-position, a carboxyl group which is esterified by a suitably substituted methyl group, such as tert.-butyl or diphenylmethyl can be split, for example, by treatment with a suitable acid agent, such as formic acid or trifluoroacetic acid, optionally with the addition of a nucleophilic compound, such as phenol or anisole, an activated esterified carboxyl group, can be split by hydrolysis for example by treatment with an acid or weakly basic aqueous agent, such as hydrochloric acid or aqueous sodium bicarbonate or an aqueous potassium phosphate buffer of pH about 7 to about 9, and an esterified carboxyl group which can be split hydrogenolytically can be split by hydrogenolysis, for example by treatment with hydrogen in the presence of a noble metal catalyst, for example a palladium catalyst.

A carboxyl group protected, for example, by silylation or stannylation can be liberated in the usual manner, for example by treatment with water or an alcohol.

Resulting compounds of the formula I can be converted in a manner which is in itself known into other compounds of the formula I.

In a resulting compound it is possible, for example, to split off an amino protective group $R_1^A$ or $R_1^b$, especially an easily removable acyl group, in a manner which is in itself known, for example an $\alpha$-polybranched lower alkoxycarbonyl group, such as tert.-butoxycarbonyl, by treatment with trifluoroacetic acid, and a 2-halogeno-lower alkoxycarbonyl group, such as 2,2,2-trichloroethoxycarbonyl or 2-iodoethoxycarbonyl or a phenacyloxycarbonyl group, by treatment with a suitable reducing metal or corresponding metal compound, for example zinc, or a chromium-II compound, such as chromium-II chloride or chromium-II acetate, advantageously in the presence of an agent which together with the metal or the metal compound generates nascent hydrogen, preferably in the presence of aqueous acetic acid. Furthermore it is possible, in a resulting compound of the formula I wherein the hydroxyl group in the 3-position is protected, preferably, for example, in the form of an esterified or etherified hydroxyl group, including a silylated hydroxyl group, to split off an acyl group $R_1^A$ or $R_1^b$, wherein optionally present free functional groups are optionally protected, amino groups, for example, in the form of acylamino groups or silylated amino groups and/or carboxyl groups, for example, in the form of esterified or silylated carboxyl groups, by treatment with an imide-halide-forming agent, reaction of the resulting imide-halide with an alcohol and splitting of the resulting iminoether.

Imide-halide-forming agents in which halogen is bonded to an electrophilic central atom are above all acid halides, such as acid bromides and especially acid chlorides. The acid halides are above all acid halides of inorganic acids, above all of acids containing phosphorus, such as phosphorus oxyhalides, phosphorus trihalides and especially phosphorus pentahalides, for example phosphorus oxychloride, phosphorus trichloride and above all phosphorus pentachloride, and also pyroactechyl-phosphorus trichloride, as well as acid halides, especially acid chlorides, of acids containing sulphur or of carboxylic acids, such as thionyl chloride, phosgene or oxalyl chloride.

The reaction with one of the imide-halide-forming agents mentioned is usually carried out in the presence of a suitable base, especially of an organic base, above all of a tertiary amine, for example a tertiary aliphatic monoamine or diamine, such as a tri-lower alkylamine, for example trimethylamine, triethylamine or ethyldiisopropylamine, also a N,N,N',N'-tetra-lower alkyl-lower alkylenediamine, for example N,N,N',N'-tetramethyl-1,5-pentylenediamine or N,N,N',N'-tetramethyl-1,6-hexylenediamine, a monocyclic or bicyclic monoamine or diamine, such as a N-substituted, for example N-lower alkylated, alkyleneamine, azaalkyleneamine or oxaalkyleneamine, for example N-methyl-piperidine or N-methyl-morpholine, as well as 2,3,4,6,7,8-hexahydro-pyrrolo[1,2-a]pyrimidine (diazabicyclononene; DBN), or a tertiary aromatic amine such as a di-lower alkylaniline, for example N,N-dimethylaniline, or above all a tertiary heterocyclic,, monocyclic or bicyclic, base, such as quinoline or isoquinoline, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; the latter can however also be present in more than or less than equimolar amount, or example in about 0.2-fold to about 1-fold amount or in, say, up to 10-fold, in particular about 3-fold to 5-fold, excess.

The reaction with the imide-halide-forming agent is preferably carried out with cooling, for example at temperatures of about −50° C to about +10° C, but it is also possible to work at higher temperatures, that is to say, for example, up to about 75° C, if the stability of the starting substances and of the products permits a higher temperature.

The imide-halide product which is usually further processed without isolation, is reacted according to the process with an alcohol, preferably in the presence of one of the above-mentioned bases, to give the imino-ether. Examples of suitable alcohols are aliphatic as well as araliphatic alcohols, above all optionally substituted, such as halogenated, for example chlorinated, lower alkanols or lower alkanols possessing additional hydroxyl groups, for example ethanol, n-propanol isopropanol or n-butanol, especially methanol, and also 2,2,2-trichloroethanol, and optionally substituted phenyl-lower alkanols, such as benzyl alcohol. Usually an excess, or example up to about 100-fold excess, of the alcohol is employed and the reaction is preferably carried out with cooling, for example at temperatures of about −50° C to about 10° C.

The imino-ether product can advantageously be split without isolation. The splitting of the imino-ether can be achieved by treatment with a suitable hydroxy compound. Preferably, water or an aqueous mixture of an organic solvent, such as an alcohol, especially a lower alkanol, for example methanol, is used. The reaction is usually carried out in an acid medium, for example at a pH value of about 1 to about 5 which can, if necessary, be obtained by adding a basic agent, such as an aqueous alkali metal hydroxide, for example sodium hydroxide or potassium hydroxide, or an acid, for example a mineral acid, or an organic acid, such as hydrochloric acid, sulphuric acid, phosphoric acid, fluoboric acid, trifluoroacetic acid or p-toluenesulphonic acid.

The three-stage process for splitting off an acyl group, described above, is advantageously carried out without isolation of the imide-halide and imino-ether intermediate products, usually in the presence of an organic solvent which is inert towards the reactants such as an optionally halogenated hydrocarbon, for example methylene chloride, and/or in an inert gas atmosphere, such as a nitrogen atmosphere.

If the imide-halide intermediate product obtainable according to the above process, instead of being reacted with an alcohol, is reacted with a salt, such as an alkali metal salt, of a carboxylic acid, especially of a sterically hindered carboxylic acid, a compound of the formula I, wherein both radicals $R_1^a$ and $R_1^b$ represent acyl groups, is obtained.

In a compound of the formula I, wherein both radicals $R_1^a$ and $R_1^b$ represent acyl groups, one of these groups, preferably the sterically less hindered group, can be removed selectively, for example by hydrolysis or aminolysis.

Certain acyl radicals $R_1^A$ of an acylamino grouping in compounds obtainable according to the invention such as, for example, the 5-amino-5-carboxy-valeryl radical, wherein carboxyl is optionally protected, for example by esterification, especially by diphenylmethyl, and/or the amino group is optionally protected, for example by acylation, especially by a halogeno-lower alkanoyl, such as dichloroacetyl, can also be split off by treatment with a nitrosilylating agent, such as nitrosyl chloride, with a carbocyclic arenediazonium salt, such as benzenediazonium chloride, or with an agent which releases positive halogen, such as N-halogeno-amide or -imide, for example N-bromosuccinimide, preferably in a suitable solvent or solvent mixture, such as formic acid, together with a nitro-or cyano-lower alkane, and treatment of the reaction product with a hydroxylic agent, such as water or a lower alkanol, for example methanol or, if in the 5-amino-5-carboxy-valeryl radical $R_1^A$ the amino group is unsubstituted and the carboxyl group is protected, for example by esterification, and $R_1^b$ preferably represents an acyl radical but can also denote hydrogen, by leaving the substance to stand in an inert solvent, such as dioxane or a halogenated aliphatic hydrocarbon, for example methylene chloride and, if necessary, working up the free or monoacylated amino compound according to methods which are in themselves known.

A triarylmethyl group, such as the trityl group $R_1^A$, can be split off, for example, by treatment with an acid agent, such as a mineral acid, for example hydrochloric acid.

Furthermore it is possible, for example in a compound of the formula I wherein $R_1^a$ and $R_1^b$ represent hydrogen and the hydroxyl group in the 3-position is preferably esterified, for example as indicated, to acylate the free amino group according to methods of acylation which are in themselves known, for example by treatment with carboxylic acids or reactive acid derivatives thereof, such as halides, for example fluorides or chlorides and also pseudohalides, such as cyanocarbonyl compounds corresponding to the acids, or anhydrides (by which there are also to be understood the internal anhydrides of carboxylic acids, that is to ketenes, or of carbamic or thiocarbamic acids, that is to say isocyanates or isothiocyanates, or mixed anhydrides, such as those which can be formed, for example, with halogenoformic acid lower alkyl esters, such as chloroformic acid ethyl esters or chloroformic acid isobutyl esters, or with trichloroacetic acid chloride), or activated esters, as well as with substituted formimino derivatives, such as substituted N,N-dimethyl-chloroformimino derivatives, or a N-substituted N,N-diacylamine, such as a N,N-diacylated aniline, the reaction being carried out, if necessary, in the presence of suitable condensation agents, when using acids, for example, in the presence of carbodiimides, such as dicyclohexylcarbodiimides and when using reactive acid derivatives, for example, in the presence of basic agents, such as triethylamine or pyridine.

An acyl group Ac can also be introduced by acylating a compound of the formula I, wherein $R_1^a$ and $R_1^b$ together represent an ylidene radical, (which can also be introduced subsequently, for example by treating a compound wherein $R_1^a$ and $R_1^b$ represent hydrogen, with an aldehyde, such as an aliphatic, aromatic or araliphatic aldehyde), for example according to the methods indicated above, and the acylation product can be hydrolysed, preferably in a neutral or weakly acid medium.

An acyl group can also be introduced stepwise. Thus, for example, it is possible to introduce into a compound of the formula I, having a free amino group, a halogeno-lower alkanoyl group, for example a bromoacetyl group, or, for example by treatment with a carbonic acid dihalide, such as phosgene, a halogenocarbonyl group, for example a chlorocarbonyl group, and to react a N-(halogeno-lower alkanoyl)-amino compound or N-(halogenocarbonyl)-amino compound thus obtainable with suitable exchange reagents, such as basic compounds, for example tetrazole, thio compounds, for example 2-mercaptro-1-methyl-imidazole, or metal salts, for example sodium azide, or alcohols, such as lower alkanols, for example tert.-butanol and thus to obtain substituted N-lower alkanoyl-amino or N-hydroxycarbonylamino compounds. Furthermore it is possible, for example, to react a compound of the formula I, wherein $R_1^a$ represents a glycyl group which is preferably substituted in the α-position, such as phenylglycl, and $R_1^b$ represents hydrogen, with an aldehyde, for example formaldehyde, or a ketone, such as a lower alkanone, for example acetone, and thus to arrive at compounds of the formula I, wherein $R_1^A$ and $R_1^b$ together represent a 5-oxo-1,3-diaza-cyclopentyl radical which is preferably substituted in the 4-position and optionally substituted in the 2-position.

In both reactants, free functional groups can transiently be protected during the acylation reaction, in a manner which is in itself known and can be liberated, after the acylation, by means of methods which are in themselves known. Thus it is preferentially possible to protect, for example, amino, hydroxyl, carboxyl or phosphono groups in the acyl radical, during the acylation reaction, for example in the form of acylamino groups, such as 2,2,2-trichloroethoxycarbonylamino, 2-bromoethoxycarbonylamino or tert.- butoxycarbonylamino groups, in the form of acyloxy groups, for example 2,2,2-trichloroethoxycarbonyloxy or 2-bromoethoxycarbonyl groups, in the form of esterified carboxyl groups, such as diphenylmethoxycarbonyl groups, or in the form of 0,0-disubstituted phosphono groups, such as 0,0-di-lower alkylphosphono groups, for example 0,0-dimethylphosphono groups, respectively, and subsequently to split such protected groups, optionally partially, and optionally after conversion of the protective group, for example a 2-bromoethoxycarbonyl group into a 2-iodoethoxycarbonyl group, the splitting being carried out, for example, by treatment with suitable reducing agents, such as zinc in the presence of aqueous acetic acid, or with trifluoroacetic acid, by hydrogenolysis or by treatment with an alkali metal halide, for example sodium iodide.

The acylation can also be effected by replacement of an already existing acyl group by another, preferably sterically hindered, acyl group, for example according to the process described above, by manufacturing the imide-halide compound treating this with a salt of an acid and splitting off hydrolytically one of the acyl groups present in the product thus obtainable, usually the sterically less hindered acyl group.

In a compound of the formula I, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-di-lower alkylsilane or tri-lower alkyl-silyl halide, for example dichloro-dimethylsilane or trimethylsilyl chloride, or by treatment with an optionally N-mono-lower alkylated, N,N-di-lower alkylated, N-tri-lower alkylsilylated or N-lower alkyl-N-tri-lower alkylsilylated N-(tri-lower alkylsilyl)-amine (see for example, British Pat. No. 1,073,530), or by treatment with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or with a tri-lower alkyl-tin halide, for example tri-n-butyl-tin chloride (see, for example, Netherlands Published Specification 67/17,107).

In a compound of the formula I which contains a free carboxyl group of the formula —C(=O)—$R_2$, such a group can be converted into a protected carboxyl group in a manner which is in itself known. Thus an ester is obtained, for example, by treatment with a suitable diazo compound, such as, for example diazomethane if necessary in the presence of a Lewis acid, such as, for example, boron trifluoride, or by reaction with an alcohol suitable for the esterification reaction, in the presence of an esterifying agent, such as a carbodiimide, for example dicyclohexylcarbodiimide, as well as carbonyldiimidazole, and also with a N,N'-disubstituted O- or S-substituted isourea or isothiourea, wherein a O-substituent and S-substituent are, for example, lower alkyl, especially tert.-butyl, pehnyl-lower alkyl or cycloalkyl, and N-substituents or N'-substituents are, for example, lower alkyl, especially isopropyl, cycloalkyl or phenyl, or according to any other known and suitable esterification process, such as reaction of a salt of the acid with a reactive ester of an alcohol and of a strong inorganic acid, or with a strong organic sulphonic acid. Furthermore, acid halides, such as acid chlorides (manufactured, for example, by treatment with oxalyl chloride), activated esters (formed, for example, with N-hydroxy-nitrogen compounds, such as N-hydroxy-succinimide), or mixed anhydrides (obtained, for example, with halogenoformic acid lower alkyl esters, such as chloroformic acid ethyl ester or chloroformic acid isobutyl ester, or with halogenoacetic acid halides, such as trichloroacetic acid chloride) can be converted into an esterified carboxyl group by reaction with alcohols, optionally in the presence of a base, such as pyridine.

In a resulting compound having an esterified grouping of the formula —C(=O)—$R_2$, this grouping can be converted into a different esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

Mixed anhydrides can be manufactured by reacting a compound of the formula I, having a free carboxyl group of the formula —C(=O)—$R_2$, preferably a salt, especially an alkali metal salt, for example a sodium salt, or ammonium salt, for example triethylammonium salt, thereof, with a reactive derivative, such as a halide, for example the chloride, of an acid, for example a halogenoformic acid lower alkyl ester or a lower alkanecarboxylic acid chloride.

In a compound obtainable according to the process, having a free carboxyl group of the formula —C(=O)—$R_2$, such a group can also be converted into an optionally substituted carbamoyl or hydrazinocarbonyl group, for which preferably reactive functionally modified derivatives, such as the above-mentioned acid halides, and generally esters, including also the abovementioned activated esters, or mixed anhydrides are reacted with ammonia or amines, including hydroxylamine, or hydrazines.

A carboxyl group protected by an organic silyl or stannyl group can be formed in a manner which is in itself known, for example by treating compounds of the formula I, wherein $R_2$ represents hydroxyl, or salts thereof, such as alkali metal salts thereof, for example sodium salts thereof, with a suitable silylating or stannylating agent, such as one of the abovementioned silylating or stannylating agents; see, for example, British Pat. No. 1,073,530 or Netherlands Published Specification No. 67/17,107.

In O-esters of compounds of the formula I the esterified hydroxyl group can be liberated in a manner which is in itself known, for example by hydrolysis, preferably in an acid or weakly basic medium, or can be converted into another esterified hydroxyl group; for example, a hydroxyl group esterified by hydrochloric acid or hydrobromic acid can be converted into a hydroxyl group esterified by hydriodic acid by treatment with an iodine salt, such as sodium iodide, in the presence of a suitable solvent, such as acetone.

It is furthermore possible to liberate modified functional substituents in groups $R_1^A$, $R_1^b$ and/or $R_2^A$, such as acylated amino groups, acylated hydroxyl groups, esterified carboxyl groups or O,O'-disubstituted phosphono groups, according to methods which are in themselves known, for example those described above, or functionally to modify free functional substituents in groups $R_1^A$, $R_1^b$ and/or $R_2^A$, such as free amino, hydroxyl, carboxyl or phosphono groups, according to processes which are in themselves known, for example acylation or esterification or substitution. Thus, for example, an amino group can be converted into a sulphoamino group by treatment with sulphur trioxide, preferably in the form of a complex with an organic base, such as a tri-lower alkylamine, for example triethylamine. Furthermore, the reaction mixture obtained by reaction of an acid addition salt of a 4-guanyl-semicarbazide with sodium nitrite can be reacted with a compound of the formula I, wherein, for example, the amino protective group $R_1^A$ represents an optionally substituted glycyl group, and the amino group can thus be converted into a 3-guanylureido group. Further, compounds with aliphatically bonded halogen, for example with an optionally substituted α-bromoacetyl grouping, can be reacted with esters of phosphorous acid, such as tri-lower alkyl-phosphite compounds, and corresponding phosphono compounds can thus be obtained.

Salts of compounds of the formula I can be manufactured in a manner which is in itself known. Thus, salts of compounds of the formula I, having a free carboxyl group, can be formed, for example, by treatment with metal compounds, such as alkali metal salts of suitable carboxylic acids, for example the sodium salt of α-ethyl-caproic acid, or with ammonia or a suitable organic amine, preferably using stoichiometric amounts or only a small excess of the salt-forming agent. Acid addition salts of compounds of the formula I having basic groupings are obtained in the customary manner, for example by treatment with an acid or with a suitable anion exchange reagent. Internal salts of compounds of the formula I which contain a salt-forming amino group and a free carboxyl group can be formed, for example, by neutralising salts, such as acid addition salts, to the isoelectric point, for example with weak bases, or by treatment with liquid ion exchangers.

Salts can be converted into the free compounds in the customary manner, metal salts and ammonium salts, for example, by treatment with suitable acids, and acid addition salts, for example by treatment with a suitable basic agent.

Resulting mixtures of isomers can be separated into the individual isomers according to methods which are in themselves known, mixtures of diastereomeric isomers, for example, by fractional crystallisation, adsorption chromatography (column chromatography or thin layer chromatography) or other suitable separation processes. Resulting racemates can be separated into the antipodes in the usual manner, if appropriate after introducing suitable salt-forming groupings, for example by forming a mixture of diastereomeric salts with optically active salt-forming agents, separating the mixture into the diastereomeric salts and converting the separated salts into the free compounds, or by fractional crystallisation from optically active solvents.

The process also encompasses those embodiments according to which compounds arising as intermediate products are used as starting substances and the remaining process steps are carried out with these, or the process is stopped at any stage; furthermore, starting substances can be used in the form of derivatives or be formed during the reaction. Furthermore, starting substances can be employed without isolation; this applies particularly to the use of the starting substances of the formula II, which are usually employed in the form of the crude reaction mixture obtainable in the course of their manufacture and are not isolated.

Preferably, those starting substances are used, and the reaction conditions are so chosen, that the compounds initially mentioned as being particularly preferred are obtained.

The starting compounds of the formula II used according to the invention can be manufactured, for example, by converting the acetoxymethyl group in a cephem compound of the formula

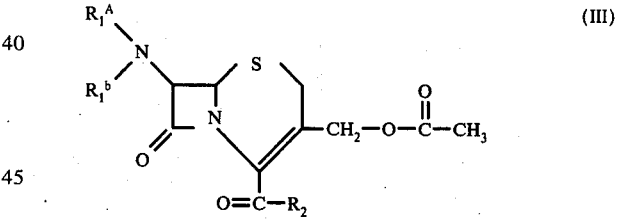

(III)

wherein $R_2$ preferably represents hydroxyl, but also represents a group $R_2^A$, into the hydroxymethyl group, for example by hydrolysis in a weakly basic medium, such as with an aqueous sodium hydroxide solution at pH 9-10, or by treatment with a suitable esterase, such as an appropriate enzyme from *Rhizobium tritolii*, *Rhizobium lupinii*, *Rhizobium japonicum* or *Bacillus subtilis*, functionally modifying a free carboxyl group of the formula —C(=O)—$R_2$ in a suitable manner, for example esterifying it by treatment with a diazo compound, such as diphenyldiazomethane, and converting the hydroxymethyl group into a halogenomethyl group, for example a chloromethyl or iodomethyl group, for example by treatment with a halogenating agent, such as a chlorinating agent, for example thionyl chloride, or an iodinating agent, such as N-methyl-N,N'-dicyclohexylcarbodiimidium iodide. A chloromethyl group is converted into the methylene group either directly, for example by treatment with a suitable chromium-II compound, such as an inorganic or organic salt of divalent chromium, for example chromium-II chloride or chromium-II acetate, in an inert solvent, such as tetrahydrofurane, or indirectly via the iodomethyl group (which can be formed, for example, by treating the chloromethyl compound with a metal iodide, such as sodium iodide, in a suitable solvent, such as acetone), by treatment of such an iodomethyl group with a suitable reducing agent, such as zinc in the presence of acetic acid. The methylene group in a compound of the formula

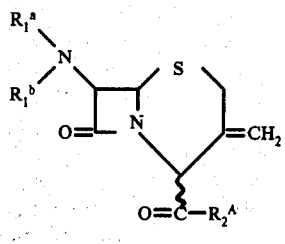 (IV)

is oxidatively degraded according to the process described below, in a cepham-3-one compound thus obtainable, in which both radicals $R_1^a$ and $R_1^b$ represent hydrogen, the free amino group can be protected by an appropriate protective group, for example by introducing an acyl group according to the process described above.

The oxidative splitting off of the methylene group in compounds of the formula IV to form an oxo group in the 3-position of the ring skeleton can be carried out in various ways.

The oxidative degradation of the methylene group in a compound of the formula IV is preferably carried out by forming an oxonide compound by treatment with ozone. Herein, ozone is preferably employed in the presence of a solvent, such as an alcohol, for example a lower alkanol, such as methanol or ethanol, a ketone, for example a lower alkanone, such as acetone, an optionally halogenated aliphatic, cycloaliphatic or aromatic hydrocarbon for example a halogeno-lower alkane, such as methylene chloride or carbon tetrachloride, or a solvent mixture, including an aqueous mixture, and with cooling or slight warming, for example at temperatures of about $-90°$ C to about $+40°$ C.

An ozonide formed as an intermediate product is split by reduction, for which it is possible to use catalytically activated hydrogen, for example hydrogen in the presence of a heavy metal hydrogenation catalyst, such as a nickel catalyst or a palladium catalyst, preferably on a suitable carrier, such as calcium carbonate or charcoal, or chemical reducing agents, such as reducing heavy metals, including heavy metal alloys or amalgams, for example zinc, in the presence of a hydrogen donor, such as an acid, for example acetic acid, or an alcohol for example a lower alkanol, reducing inorganic salts, such as alkali metal iodides, for example sodium iodide, in the presence of a hydrogen donor, such as an acid, for example acetic acid, or reducing organic compounds, such as formic acid, a reducing sulphide compound such as a di-lower alkylsulphide, for example dimethylsulphide, a reducing organic phosphorus compound, such as a phosphine, which can optionally contain substituted aliphatic or aromatic hydrocarbon radicals as substituents, such as tri-lower alkyl-phosphines, for example tri-n-butylphosphine, or triarylphosphines, for example tri-phenylphosphine, also phosphites which contain optionally substituted aliphatic hydrocarbon radicals as substituents, such as tri-lower alkylphosphites, usually in the form of corresponding alcohol adduct compounds, such as trimethylphosphite, or phosphorous acid triamides which contain optionally substituted aliphatic hydrocarbon radicals as substituents, such as hexa-lower alkylphosphorous acid triamides, for example hexamethylphosphorous acid triamide, the latter preferably in the form of a methanol adduct, or tetracyanoethylene. The splitting of the oxonide, which is usually not isolated, is normally carried out under the conditions which are employed for its manufacture, that is to say in the presence of a suitable solvent or solvent mixture, and with cooling or slight warming.

Depending on how the oxidation reaction is carried out, according to the process a compound of the formula II or the corresponding 1-oxide or a mixture of the two compounds is obtained. Such a mixture can be separated into the compound of the formula I and the corresponding 1-oxide or can be oxidised to the pure 1-oxide of a compound of the formula I.

As mentioned above, the new compounds of the formula I can be used as intermediate products for the manufacture of compounds having the cephem structure, which either possess valuable pharmacological properties or can in turn be used as intermediate products.

Thus it is possible to convert compounds of the formula I or their O-esters, by splitting off water or an acid under acid or basic conditions, into the known 3-cephem compounds of the formula

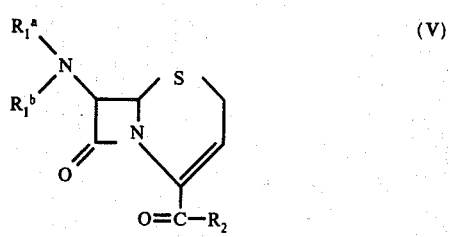 (V)

wherein $R_1^a$, $R_1^b$ and $R_2$ have the above meanings, and in which these radicals can be converted into one another in a manner which is in itself known. The compounds of the formula V or salts thereof either display valuable pharmacological, especially anti-microbial properties; in particular, those in which $R_1^a$ represents an acyl radical contained in pharmacologically active N-acyl derivatives of 6β-amino-penam-3-carboxylic acid compounds and 7β-amino-3-cephem-4-carboxylic acid compounds, $R_1^b$ denotes hydrogen and $R_2$ represents hydroxyl or an etherified hydroxyl group which, together with the carbonyl grouping forms a carboxyl group which can be split under physiological conditions, or salts thereof, are active against micro-organisms, such as Gram-positive bacteria, for example *Staphylococcus aureus*, (for example in mice at doses of about 0.001 to about 0.02 g/kg administered orally) and Gram-negative bacteria, for example *Escherichia coli* (for example in mice at doses of about 0.001 to about 0.05 g/kg administered orally) and also against *Klebsiella pneumoniae*, *Proteus vulgaris* or *Salmonella typhosa*, in particular also against penicillin-resistant bacteria, and can therefore be used correspondingly, for example in the form of antibiotically active preparations. Further, compounds of the formula V can be used as intermediate products for the manufacture of the compounds mentioned having pharmacological properties. Compounds of this nature are described, for example, in German Offenlegungsschrift No. 2,151,567.

In the above conversion of compounds of the formula I and O-esters thereof into compounds of the formula V, compounds of the formula I and in particular O-esters thereof do not have to be isolated; they can be directly converted, in the form of the crude reaction mixtures obtained from their manufacture, into the compounds of the formula V.

In the context of the present description, the organic radicals described as "lower" contain up to 7, preferably up to 4, carbon atoms; acyl radicals contain up to 20, preferably up to 12, carbon atoms.

The examples which follow serve to illustrate the invention.

EXAMPLE 1

A solution of 1.0 g of 3-methylene-7β-phenylacetylamino-cepham-4α-carboxylic acid diphenylmethyl ester in 100 ml of methanol is treated with an oxygen-ozone mixture at −70° C until a blue colouration begins to show, and the excess ozone is expelled with nitrogen. The reaction mixture is treated with 0.4 ml of dimethylsulphide and is stirred for 30 minutes at room temperature. It is then cooled to 0° C and a solution of 0.10 g of sodium borohydride in 5 ml of water is added to the reaction mixture, which contains 7β-phenylacetylamino-capnam-3-one-4α-carboxylic acid diphenylmethyl ester and 7β-phenylacetylamino-cepham-3-one-4α-carboxylic acid diphenylmethyl ester-1-oxide. The reaction is allowed to proceed for 30 minutes at 0° C, the pH value is adjusted to about 6 by adding acetic acid and the reaction mixture is evaporated under reduced pressure. The residue is taken up in ethyl acetate; the organic solution is washed with a saturated aqueous sodium bicarbonate solution and a saturated aqueous sodium chloride solution, dried over sodium sulphate and evaporated under reduced pressure. The residue is chromatographed on 50 g of silica gel. 3ξ-Hydroxy-7β-phenylacetylamino-cepham-4α-carboxylic acid diphenylmethyl ester is eluted with a 2:1 mixture of toluene and ethyl acetate and after crystallisation from a mixture of acetone and diethyl ether melts at 157°–160° C; $[\alpha]_D = +80° \pm 1°$ (c = 0.492 in dioxane): $\lambda_{max} = 258\mu$ ($\epsilon = 850$); infrared absorption spectrum (in methylene chloride): characteristic bands at 2.82μ, 2.94μ, 5.63μ, 5.74μ, 5.92μ, 6.25μ and 6.63μ.

3ξ-Hydroxy-7β-(D-α-tert.-butoxycarbonylamino-α-phenylacetylamino)-cepham-4α-carboxylic acid diphenylmethyl ester is obtained analogously by ozonising 3-methylene-7β-(D-α-tert.-butoxycarbonylamino-α-phenylacetylamino)-cepham-4α-carboxylic acid diphenylmethyl ester, followed by treatment with dimethylsulphide and reduction of the 7β-(D-α-tert.-butoxycarbonylamino-α-phenylacetylamino)-cepham-3-one-4α-carboxylic acid diphenylmethyl ester or its mixture with the corresponding 1-oxide compound by means of sodium borohydride; in the compound thus obtainable, the esterified carboxyl groups and the acylated α-amino group can be liberated by treatment with trifluoroacetic acid in the presence of anisole and the 3ξ-hydroxy-7β-(D-α-phenyl-glycylamino)cepham-4α-carboxylic acid can thus be obtained.

The starting material can be manufactured as follows.

A solution of 11.82 g of the crude sodium salt of 3-hydroxymethyl-7β-phenylacetylamino-3-cephem-4-carboxylic acid (manufactured by enzymatic desacetylation of the sodium salt of 3-acetoxymethyl-7β-phenylacetylamino-3-cephem-4-carboxylic acid with the aid of a purified enzyme extract from *Bacillus subtilis*, strain ATCC 6,633, and subsequent lyophilisation of the reaction solution) in 200 ml of water is covered with 400 ml of ethyl acetate and acidified to a pH value of 2 with concentrated aqueous phosphoric acid. The aqueous phase is separated off and twice re-extracted with 150 ml of ethyl acetate at a time. The combined organic extracts are washed four times with 50 ml of water at a time, dried over magnesium sulphate and then concentrated to about 400 ml. Excess diphenyl-diazomethane is added to the solution, which is left to stand for 3 hours at room temperature, and the granular crystalline precipitate is then filtered off. The filtrate is concentrated to about 200 ml, cyclohexane is added whilst warm and after cooling to room temperature the mixture is left to stand for some time at about 4° C. The precipitate is filtered off and recrystallised from a mixture of acetone and cyclohexane; the 3-hydroxymethyl-7β-phenylacetylamino-3-cephem-4-carboxylic acid diphenylmethyl ester thus obtained melts at 176°–176.5° C (uncorrected); $[\alpha]_D^{20} = -6° \pm 1°$ (c = 1.231% in chloroform); thin layer chromatogram (silica gel; detection with iodine vapour or ultraviolet light, $\lambda_{254\ m\mu}$); Rf = 0.42 (system: chloroform/acetone, 4:1), Rf = 0.43 (system: toluene/acetone, 2:1), and Rf = 0.41 (system: methylene chloride/acetone, 6:1).

1.03 g of 3-hydroxymethyl-7β-phenylacetylamino-3-cephem-4-carboxylic acid diphenylmethyl ester and 1.05 g of N-methyl-N,N'-dicyclohexylcarbodiimidium iodide are dissolved in 25 ml of absolute tetrahydrofurane under a nitrogen atmosphere and warmed at 35° C for one hour. Thereafter, a further 1.05 g of N-methyl-N,N'-dicyclohexylcarbodiimidium iodide, in 15 ml of absolute tetrahydrofurane, is added and the mixture is left to stand for 17 hours at room temperature under a nitrogen atmosphere. The reaction mixture is freed of the solvent on a rotary evaporator under reduced pressure. The residue is taken up in methylene chloride and filtered through a column of 50 g of silica gel (with addition of 10% of distilled water); the column is rinsed with 4 portions of methylene chloride, each of 100 ml. The eluate is concentrated to a small volume and chromatographed on a silica gel column (90 g; deactivated by adding 10% of distilled water). Non-polar impurities are eluted with a total of 900 ml of a 3:7 mixture of toluene and methylene chloride. Elution with 2 portions of methylene chloride, each of 200 ml, yields 3-iodomethyl-7β-phenylacetylamino-3-cephem-4-carboxylic acid diphenylmethyl ester; the fractions which according to a thin layer chromatogram are a single substance are lyophilised from benzene. Infrared absorption spectrum (in methylene chloride): characteristic bands at 3.00 $\mu$, 5.62 $\mu$, 5.82$\mu$, 5.95 $\mu$, 6.70 $\mu$, 7.32 $\mu$ and 8.16 $\mu$.

The iodination reagent used above can be manufactured as follows.

42 g of freshly distilled N,N'-dicyclohexylcarbodiimide are dissolved in 90 ml of methyl iodide in a 250 ml round flask equipped with a magnetic stirrer and reflux condenser and fitted nitrogen bulb, at room temperature under a nitrogen atmosphere, and the colourless reaction mixture is stirred for 72 hours at a bath temperature of 70° C. At the end of the reaction time, the excess methyl iodide is distilled from the solution, which is now red-brown, under reduced pressure and the viscous red-brown residue is dissolved in 150 ml of absolute toluene at 40° C. The crystal mass, which crystallises out spontaneously within a few hours, is separated from the mother liquor with the aid of a glass suction filter with fitted nitrogen bulb, whilst excluding air, the reaction vessel is rinsed three times with 25 ml of absolute, ice-cold toluene at a time and the same toluene is used in order to wash the slightly yellowish crystal mass on the glass suction filter until it is colourless. After drying for 20 hours at 0.1 mm Hg and room temperature, the N-methyl-N,N'-dicyclohexylcarbodiimidium iodide is obtained in the form of colourless crystals, melting point 111°–113° C; infrared absorption spectrum (in chloroform): characteristic bands at 4.72 $\mu$ and 6.00 $\mu$.

A solution of 0.400 g of 3-iodomethyl-7β-phenylacetylamino-3-cephem-4-carboxylic acid diphenylmethyl ester in 15 ml of 90% strength aqueous acetic acid is cooled to 0° C in an ice bath and 2.0 g of zinc dust are added in portions whilst stirring well. After a reaction time of 30 minutes at 0° C the unreacted zinc dust is filtered off by means of a suction filter covered with a layer of diatomaceous earth; the filter residue is repeatedly suspended in fresh methylene chloride and again filtered. The combined filtrates are concentrated under reduced pressure, mixed with absolute toluene and evaporated to dryness under reduced pressure. The residue is taken up in 50 ml of methylene chloride and 30 ml of an 0.5 molar aqueous dipotassium hydrogen phosphate solution, whilst stirring; the aqueous phase is separated off, re-extracted with two portions of methylene chloride, each of 30 ml, and discarded. The organic extracts are repeatedly washed with a saturated aqueous sodium chloride solution, dried over magnesium sulphate and evaporated under reduced pressure. The residue is chromatographed on a column of 22 g of silica gel (with addition of 10% of water). The 3-methylene-7β-phenylacetylamino-cepham-4α-carboxylic acid diphenylmethyl ester is eluted with methylene chloride, and with methylene chloride containing 2% of methyl acetate, and is crystallised from a mixture of methylene chloride and hexane, melting point 144°–147° C; $[\alpha]_D^{20} = -18° \pm 1°$ (c = 0.715 in chloroform); ultraviolet absorption spectrum (in 95% strength aqueous ethanol): $\lambda_{max}$ = 254 m$\mu$ ($\beta$ = 1,540) and 260 m$\mu$ ($\epsilon$ = 1,550); infrared absorption spectrum (in methylene chloride): characteristic bands at 2.94 $\mu$, 5.65 $\mu$, 5.74 $\mu$, 5.94 $\mu$, 6.26 $\mu$ and 6.67 $\mu$.

EXAMPLE 2

A mixture of 0.312 g of 3ξ-hydroxy-7β-phenylacetylamino-cepham-4α-carboxylic acid diphenylmethyl ester in 15 ml of pyridine and 7 ml of acetic anhydride is left to stand for 16 hours at 0° C and after addition of 50 ml of toluene is evaporated under reduced pressure. The residue is taken up in ethyl acetate; the organic solution is washed with a saturated aqueous sodium bicarbonate solution and a saturated aqueous sodium chloride solution, dried over sodium sulphate and evaporated under reduced pressure. The residue is purified by means of preparative thin layer chromatography; a silica gel plate of 100 cm length is used and development is carried out with a 1:1 mixture of toluene and ethyl acetate. 3ξ-Acetoxy-7β-phenylacetylaminocepham-4α-carboxylic acid diphenylmethyl ester of Rf = 0.47 is obtained, melting at 162°–164° C after crystallisation from a mixture of methylene chloride and pentane; $[\alpha]_D^{20} = +55° \pm 1°$ (c = 0.492 in chloroform); ultraviolet absorption spectrum (in 95% strength ethanol): $\lambda_{max}$ = 253 m$\mu$ ($\epsilon$ = 700), 258 m$\mu$ ($\epsilon$ = 820) and 265 m$\mu$ ($\epsilon$ = 660): infrared absorption spectrum (in methylene chloride): characteristic bands at 2.96$\mu$, 5.66$\mu$, 5.77$\mu$, 5.97$\mu$, 6.28$\mu$ and 6.71$\mu$.

Treatment of 3ξ-hydroxy-7β-(D-α-tert.-butoxycarbonylamino-α-phenylacetylamino)-cepham-4α-carboxylic acid diphenylmethyl ester with acetic anhydride in the presence of pyridine yields 3ξ-acetoxy-7β-(D-α-tert.-butoxycarbonylamino-α-phenylacetylamino)-cepham-4α-carboxylic acid diphenylmethyl ester, in which the carboxyl group and the α-amino group can be liberated by treatment with trifluoroacetic acid in the presence of anisole; 3ξ-acetoxy-7β-(D-α-phenylglycylamino)-cepham-4α-carboxylic acid is thus obtained.

EXAMPLE 3

A mixture of 0.150 g of 3ξ-acetoxy-7β-phenylacetylamino-cepham-4α-carboxylic acid diphenylmethyl ester and 5 ml of methylene chloride is treated with 0.1 ml of triethylamine and left to stand for 16 hours at room temperature. The reaction mixture is diluted with 100 ml of methylene chloride; the organic phase is washed with 50 ml of 2 N hydrochloric acid and 50 ml of a saturated aqueous sodium chloride solution, dried over magnesium sulphate and evaporated under reduced pressure. The residue is purified by means of preparative thin layer chromatography (2 silica gel plates of 20 cm length, system: toluene/ethyl acetate, 3:1). At Rf = 0.36, a pale yellowish oil is obtained, which crystallises from a mixture of methylene chloride and hexane. The product is 7β-phenylacetylamino-3-cephem-4-carboxylic acid diphenylmethyl ester, melting point 161°–163° C, $[\alpha]_D^{20}$ = +30° ± 1° (c = 0.968 in dioxane); thin layer chromatogram (silica gel; identification in ultraviolet light and by means of iodine vapour): Rf = 0.55 (system: toluene-/acetone, 4:1), Rf = 0.35 (system: toluene/acetone, 9:1) and Rf = 0.40 (system: toluene/ethyl acetate, 4:1): ultraviolet absorption spectrum: $\lambda_{max}$ = 258 mμ ($\epsilon$ = 6,100) and $\lambda_{min}$ = 240 mμ ($\epsilon$ = 5,250) (in methylene chloride) and $\lambda_{max}$ = 259 mμ ($\epsilon$ = 6,050) and $\lambda_{min}$ = 239 mμ ($\epsilon$ = 4,950) (in 95% strength aqueous ethanol); infrared absorption spectrum: characteristic bands at 2.90μ, 5.57μ, 5.76μ, 5.91μ, 6.09μ, 6.66μ, 7.13μ, 8.12μ, 8.63μ, 9.07μ, 10.43μ and 12.22μ (in methylene chloride) and 3.01μ, 5.60μ, 5.82μ, 6.04μ, 6.08μ (shoulder), 6.51μ and 7.13μ (in mineral oil).

EXAMPLE 4

A solution of 0.566 g of 7β-phenylacetylamino-3-cephem-4-carboxylic acid diphenylmethyl ester in 2.5 ml of anisole and 10 ml of trifluoroacetic acid is left to stand for 20 minutes at room temperature and is then evaporated to dryness repeatedly, with addition of toluene, until the trifluoroacetic acid has been completely removed. The residue is taken up in ethyl acetate and 0.5 molar aqueous dipotassium hydrogen phosphate solution and the phases are separated. The aqueous phase is twice washed with ethyl acetate and the organic solution is twice washed with 0.5 molar aqueous dipotassium hydrogen phosphate solution. The combined aqueous solutions are covered with fresh ethyl acetate and acidified with 20% strength aqueous phosphoric acid. They are extracted with ethyl acetate and the organic solution is washed with a saturated aqueous sodium chloride solution, dried over magnesium sulphate and evaporated to dryness under reduced pressure. The residue is chromatographed on a 50-fold amount of silica gel (washed with concentrated hydrochloric acid) and 7β-phenylacetylamino-3-cephem-4-carboxylic acid is eluted with methylene chloride, containing 10–20% of methyl acetate. The fractions which, according to thin layer chromatography, are a single substance, are crystallised from a mixture of methyl acetate and cyclohexane; the colourless crystals melt at 190° – 191° C; thin layer chromatogram (silica gel; developing with iodine vapour or identification under ultraviolet light): Rf = 0.58 (system: n-butanol/acetic acid/water, 75:7.5:21), Rf = 0.265 (system: n-butanol-/ethanol/water, 40:10:50), Rf = 0.53 (system: n-butanol/acetic acid/water, 40:10:40), Rf = 0.43 (system: ethyl acetate/pyridine/acetic acid/water, 62:21:6:11) and Rf = 0.43 (system: ethyl acetate/n-butanol/pyridine/acetic acid/water, 42:21:21:6:10).

EXAMPLE 5

A solution of 1.94 g of 7β-phenylacetylamino-3-cephem-4-carboxylic acid diphenylmethyl ester in 100 ml of absolute methylene chloride is cooled −15° C, 3.86 ml of absolute pyridine and 31.6 ml of an 8% strength solution of phosphorus pentachloride in methylene chloride are then added and the reaction mixture is stirred for 30 minutes at −10° C and for a further 30 minutes at −5° C. The golden yellow solution is cooled to −20° C and 26.8 ml of absolute methanol are added at a speed such that the internal temperature does not rise above −10° C. The reaction mixture is stirred for one hour at −10° C and left to stand for a further hour at 25°–30° C, and is then mixed with 80 ml of an 0.5 molar aqueous potassium dihydrogen phosphate solution, whilst stirring vigorously. The pH value of the two-phase reaction mixture is adjusted to 2 by dropwise addition of 20% strength phosphoric acid, the mixture is stirred for 20 minutes at room temperature and the phases are separated. The aqueous solution is twice washed with methylene chloride; the combined organic solutions are washed with two portions of water, each of 20 ml, and are dried over anhydrous magnesium sulphate.

The solvent is removed under reduced pressure; the oily residue is applied to a column of 110 g of silica gel (5% water content). The elution with methylene chloride, phenylacetic acid methyl ester and methylene chloride containing 3% of methyl acetate yields 7β-amino-3-cephem-4-carboxylic acid diphenylmethyl ester, which is crystallised by dissolving in a small amount of methylene chloride and adding diethyl ether to the warm solution (giving needle-shaped crystals), and is washed with cold diethyl ether and dried, melting point 153° – 154° C; thin layer chromatogram (silica gel): RF = 0.50 (system: toluene/acetone, 4:1), Rf = 0.65 (system: toluene/acetone, 2:1), Rf = 0.40 (system: toluene/ethyl acetate, 1:1) and Rf = 0.33 (system: toluene/diethyl ether, 1:1); ultraviolet absorption spectrum: $\lambda_{max}$ = 257 mμ ($\epsilon$ = 8,150) and $\lambda_{min}$ = 245 mμ ($\epsilon$ = 7,730) (in methylene chloride) and $\lambda_{max}$ = 255 mμ ($\epsilon$ = 5,500) and $\lambda_{min}$ = 236 mμ ($\epsilon$ = 4,650) (in 95% ethanol); infrared absorption spectrum: characteristic bands at 2.91μ, 2.97μ, 5.61μ. 5.78μ, 6.11μ, 7.14μ, 8.15μ, 8.29, 9.14μ and 9.83μ (in methylene chloride) and at 2.99μ, 5.65μ, 5.77μ. 6.08μ, 7.14μ, 7.74μ, 7.84μ, 8.08μ, 8.53μ, 9.14μ, 9.85μ and 10.35 (in mineral oil).

EXAMPLE 6

0.380 g of 7β-amino-3-cephem-4-carboxylic acid diphenylmethyl ester is covered with 2 ml of anisole and 8 ml of absolute trifluoroacetic acid, and the clear solution is left to stand for 10 minutes at room temperature and is then diluted with about 20 ml of absolute toluene. The mixture is evaporated under reduced pressure; the residue is twice evaporated to dryness after addition of toluene and is then suspended in 5 ml of methanol, 5 ml of diethyl ether and 0.5 ml of water. The pH value of the suspension is adjusted to 3.5 by dropwise addition of a 5% strength solution of triethylamine in methanol; the whole is left to stand for 30 minutes in an ice bath and the fine precipitate is filtered off with the aid of a suitable glass suction filter. The pale beige-coloured filter residue is washed with a mixture of methanol and methylene chloride and then with diethyl ether and is dried under reduced pressure at 35° C. The 7β-amino3-cephem-4-carboxylic acid thus obtainable as a fine microcrystalline powder decomposes at 215° C; thin layer chromatogram (silica gel; developing with iodine): Rf = 0.12 (system: n-butanol/acetic acid/water, 67:10:23), Rf = 0.28 (system: n-butanol/-pyridine/acetic acid/water, 40:24:6:30) and Rf = 0.21 (system: ethyl acetate/n-butanol/pyridine/acetic acid/-water, 42:21:21:6:10); infrared absorption spectrum (in mineral oil): characteristic bands at 3.12μ, 3.80μ. 4.12μ (shoulder), 4.92μ, 5.54μ, 6.05μ (shoulder), 6.19μ, 6.55μ, 7.05μ, 7.42μ, 8.23μ, 8.79μ, 9.55μ, 12.08μ, 12.69μ and 13.04μ.

EXAMPLE 7

A suspension of 0.070 g of 7β-amino-3-cephem-4-carboxylic acid in 2 ml of absolute methylene chloride is treated with 0.031 g of triethylamine in 0.35 ml of methylene chloride, the suspension is diluted with 5 ml of absolute tetrahydrofurane and the mixture is stirred for 30 minutes, periodically in an ultrasonics bath.

0.102 g of tert.-butoxycarbonyl-D-α-phenylglycine is dissolved in 5 ml of absolute methylene chloride, 0.040 g of 4-methylmorpholine is added and the mixture is diluted with 10 ml of acetonitrile. It is cooled to −20° C and 0.060 g of chloroformic acid isobutyl ester is added whilst stirring, after which the reaction is allowed to proceed for 30 minutes at −15° C. After again cooling to below −20° C, the milky suspension of the triethylammonium salt of 7β-amino-3-cephem-4-carboxylic acid is then added. The reaction mixture is stirred for 30 minutes at −15° C, a further 30 minutes at 0° C and finally 2 hours at room temperature. It is filtered, the residue is rinsed with acetonitrile, methylene chloride and diethyl ether, and the filtrate is dried and evaporated to dryness. The residue is taken up in ethyl acetate and water and the mixture is acidified to pH 2 by adding 5 molar aqueous phosphoric acid whilst stirring vigorously and cooling with ice. The organic phase is separated off and washed four times with a small amount of a saturated aqueous sodium chloride solution. The aqueous extracts are re-extracted with 2 portions of ethyl acetate and the combined organic extracts are dried over anhydrous magnesium sulphate and freed of the solvent under reduced pressure. The residue is chromatographed on 10 g of silica gel (column; 5% water added). First, unreacted tert.-butoxycarbonyl-D-α-phenylglycine is eluted with methylene chloride and with methylene chloride containing increasing proportions of acetone, and subsequently 7β-[N-(N-tert.-butoxycarbonyl-D-α-phenylglycyl)-amino]-3-cephem-4-carboxylic acid is eluted and obtained in an amorphous form; ultraviolet absorption spectrum (in 95% strength ethanol): $\lambda_{max} = 252$ mμ ($\epsilon = 5,100$); infrared absorption spectrum (in methylene chloride): characteristic bands at 5.61μ, 5.85μ, 5.92μ and 6.12μ; thin layer chromatogram (silica gel G; detection with iodine vapour): Rf = 0.6–0.7 (system: n-butanol/acetic acid/water, 44:12:44).

EXAMPLE 8

A solution of 0.02 g of 7β-[N-(N-tert.-butoxycarbonyl-D-α-phenylglycyl)-amino]-3-cephem-4-carboxylic acid in 3 ml of pure trifluoroacetic acid is left to stand for 15 minutes at room temperature. The resulting solution is evaporated in a rotary evaporator and the residue is twice evaporated to dryness with addition of 20 ml of a 1:1 mixture of chloroform and toluene, in order to remove the trifluoroacetic acid completely, and is dried for 16 hours at 0.0001 mm Hg. 7β-[N-(D-α-Phenylglycyl)-amino]-3-cephem-4-carboxylic acid is obtained as a yellowish amorphous powder, by adding an equivalent amount of triethylamine to a solution of the resulting salt with trifluoroacetic acid, in water and methanol, evaporating and digesting the residue with methylene chloride. Thin layer chromatogram (silica gel; developing with iodine vapour): Rf = 0.29 (system: n-butanol/pyridine/acetic acid/water, 40:24:6:30); ultraviolet absorption spectrum (in water): $\lambda_{max} = 250$ mμ ($\epsilon = 4,300$).

EXAMPLE 9

The following compounds can be obtained analogously if suitable starting substances are chosen and, if necessary, after additional conversions have been carried out:

7β-Phenylacetylamino-3-cephem-4-carboxylic acid 4,4'-dimethoxy-diphenylmethyl ester; by oxidation of 3-methylene-7β-phenylacetylamino-cepham-4α-carboxylic acid 4,4'-dimethoxydiphenylmethyl ester with ozone, followed by treatment with dimethylsulphide, reduction of the keto group in 7β-phenylacetylamino-cepham-3-one-4α-carboxylic acid 4,4'-dimethoxydiphenylmethyl ester with sodium borohydride, acetylation of the 3-hydroxyl group in 3ξ-hydroxy-7β-phenylacetylaminocepham-4α-carboxylic acid 4,4'-dimethoxy-diphenylmethyl ester with acetic anhydride in the presence of pyridine, and treatment of 3ξ-acetoxy-7β-phenylacetylamino-cepham-4α-carboxylic acid 4,4'-dimethoxy-diphenylmethyl ester with triethylamine.

7β-Phenylacetylamino-3-cephem-4-carboxylic acid benzyl ester; by oxidation of 3-methylene-7β-phenylacetylamino-cepham-4α-carboxylic acid benzyl ester with ozone, followed by treatment with dimethylsulphide, reduction of the keto group in 7β-phenylacetylamino-cepham-3-one-4α-carboxylic acid benzyl ester with sodium borohydride, acetylation of the 3-hydroxyl group in 3ξ-hydroxy-7β-phenylacetylamino-cepham-4α-carboxylic acid benzyl ester with acetic anhydride in the presence of pyridine and treatment of 3ξ-acetoxy-7β-phenylacetylamino-cepham-4α-carboxylic acid benzyl ester with triethylamine.

7β-Phenoxyacetylamino-3-cephem-4-carboxylic acid, thin layer chromatogram (silica gel): Rf = 0.4–0.5 (system: n-butanol/acetic acid/water, 75:7.5:21); by oxidation of 3-methylene-7β-phenoxyacetylamino-cepham-4α-carboxylic acid diphenylmethyl ester with ozone, followed by treatment with dimethylsulphide, reduction of the keto group in 7β-phenoxyacetylamino-cepham-3-one-4α-carboxylic acid diphenylmethyl ester with sodium borohydride, acetylation of the 3-hydroxyl group in 3ξ-hydroxy-7β-phenoxyacetylamino-cepham-4α-carboxylic acid diphenylmethyl ester with acetic anhydride in the presence of pyridine and treatment of 3ξ-acetoxy-7β-phenoxyacetylamino-cepham-4α-carboxylic acid diphenylmethyl ester with triethylamine, followed by liberation of the acid by treatment with trifluoroacetic acid and anisole.

7β-(2-Thienyl-acetylamino)-3-cephem-4-carboxylic acid, thin layer chromatogram (silica gel): Rf = 0.5–0.6 (system: n-butanol/pyridine/acetic acid/water, 38:24:8:30); ultraviolet absorption spectrum (in 0.1 molar aqueous sodium bicarbonate solution); $\lambda_{max}$ at 237 mμ; infrared absorption spectrum (in mineral oil): characteristic band at 5.62μ; by oxidation of 3-methylene-7β-(2-thienyl-acetylamino)cepham-4α-carboxylic acid diphenylmethyl ester with ozone, followed by treatment with dimethylsulphide, reduction of the keto group in 7β-(2-thienyl-acetylamino)-cepham-3-one-4α-carboxylic acid diphenylmethyl ester with sodium borohydride, acetylation of the 3-hydroxyl group in 3ξ-hydroxy-7β-(2-thienyl-acetylamino)-cepham-4α-carboxylic acid diphenylmethyl ester with acetic anhydride in the presence of pyridine and treatment of 3ξ-acetoxy-7β-(2-thienyl-acetylamino)-cepham-4α-carboxylic acid diphenylmethyl ester with triethylamine, followed by liberating the acid by treatment with trifluoroacetic acid and anisole.

7β-(1-Tetrazolyl-acetylamino)-3-cephem-4-carboxylic acid, thin layer chromatogram (silica gel): Rf = 0.4–0.5 (system: n-butanol/pyridine/acetic acid/water, 42:24:4:30); ultraviolet absorption spectrum (in methanol): $\lambda_{max}$ at 255 mμ; by oxidation of 3-methylene-7β-(1-tetrazolylacetylamino)-3-cepham-4α-carboxylic acid diphenylmethyl ester with ozone, followed by treatment with dimethylsulphide, reduction of the keto group in 7β-(1-tetrazolyl-acetylamino)cepham-3-one-4α-carboxylic acid diphenylmethyl ester with sodium borohydride, acetylation of the 3-hydroxyl group in 3ξ-hydroxy-7β-(1-tetrazolyl-acetylamino)-cepham-4α-carboxylic acid diphenylmethyl ester with acetic anhydride in the presence of pyridine and treatment of 3ξ-acetoxy-7β-(1-tetrazolyl-acetylamino)-cepham-4α-carboxylic acid diphenylmethyl ester with triethylamine, followed by liberating the acid by treatment with trifluoroacetic acid and anisole.

7β-(1-Methyl-2-imidazolylthio-acetylamino)-3-cephem-4-carboxylic acid, thin layer chromatogram (silica gel): Rf=0.3–0.4 (system: n-butanol/pyridine/acetic acid/water, 42:24:4:30); ultraviolet absorption spectrum (in methanol): $\lambda_{max}$ at 252 mμ; by oxidation of 3-methylene-7β-(1-methyl-2-imidazolylthio-acetylamino)-3-cepham-4-α-carboxylic acid diphenylmethyl ester with ozone, followed by treatment with dimethylsulphide, reduction of the keto group in 7β-(1-methyl-2-imidazolylthio-acetylamino)-cepham-3-one-4-α-carboxylic acid diphenylmethyl ester with sodium borohydride, acetylation of the 3-hydroxyl group in 3ξ-hydroxy-7β-(1-methyl-2-imidazolylthio-acetylamino)-cepham-4α-carboxylic acid diphenyl ester with acetic anhydride in the presence of pyridine and treatment of 3ξ-acetoxy-7-β-(1-methyl-2-imidazolylthio-acetylamino)-cepham-4α-carboxylic acid diphenylmethyl ester with triethylamine, followed by liberation of the acid by treatment with trifluoroacetic acid an anisole.

7β-(D-α-Hydroxy-α-phenylacetylamino)-3-cephem-4-carboxylic acid, melting point 184° – 187° C (with decomposition) after recrystallisation from a mixture of methyl acetate and diethyl ether and drying in a high vacuum at 45° C for 24 hours; thin layer chromatography (silica gel): Rf = 0.51 (system: n-butanol/acetic acid/water, 75:7.5:21), Rf = 0.25 (system: n-butanol/ethanol/water, 40:10:50), Rf = 0.56 (system: n-butanol/acetic acid/water, 44:12:44), Rf = 0.32 (system: ethyl acetate/pyridine/acetic acid/water, 62:21:6:11) and Rf = 0.51 (system: n-butanol/pyridine/acetic acid/water, 38:24:8:30); $[\alpha]_D = +72° \pm 1°$ (c = 1.079 in dioxane); ultraviolet absorption spectrum (in 95% strength aqueous ethanol): $\lambda_{max}$ = 254 mμ ($\epsilon$ = 5,450) and $\lambda_{min}$ = 238 mμ ($\epsilon$ = 5,280); infrared absorption spectrum (in mineral oil): characteristic bands at 2.83μ, 3.00μ, 5.67μ, 5.93μ (shoulder), 5.96μ, 6.16μ, 6.75μ, 8.03μ, 8.30μ, 9.04μ, 9.25μ, 9.45μ, 12.33μ, 13.05μ, 13.38μ, 13.57μ and 14.23μ; by oxidation of 3-methylene-7β-(D-α-phenyl-α-2,2,2-trichloroethoxycarbonyloxyacetylamino)-cepham-4α-carboxylic acid diphenylmethyl ester with ozone, followed by treatment with dimethylsulphide, reduction of the keto group in 7β-(D-α-phenyl-α-2,2,2-trichloroethoxycarboxy-acetylamino)-cepham-3-one-4α-carboxylic acid diphenylmethyl ester with sodium borohydride, acetylation of the 3-hydroxyl group in 3ξ-hydroxy-7β-(D-α-phenyl-2,2,2-trichloroethoxycarboxy-acetylamino)-cepham-4α-carboxylic acid diphenylmethyl ester with acetic anhydride in the presence of pyridine and treatment of the 3ξ-acetoxy-7β-(D-α-phenyl-α-2,2,2-trichloroethoxycarboxy-acetylamino)cepham-4α-carboxylic acid diphenylmethyl ester with triethylamine, followed by liberation of the acid by treatment with trifluoroacetic acid and anisole, and liberation of the hydroxyl group by treatment with zinc and 90% strength aqueous acetic acid.

7β-(4-Pyridylthio-acetylamino)-3-cephem-4-carboxylic acid, amorphous product; thin layer chromatogram (silica gel): Rf = 0.35–0.45 (system: n-butanol/pyridine/acetic acid/water, 42:24:4:30); infrared absorption spectrum (in mineral oil): characteristic band at 5.62μ; by oxidation of 3-methylene-7β-(4-pyridylthio-acetylamino)-cepham-4α-carboxylic acid diphenylmethyl ester with ozone, followed by treatment with dimethylsulphide, reduction of the keto group in 7β-(4-pyridylthio-acetylamino)-cepham-3-one-4α-carboxylic acid diphenylmethyl ester with sodium borohydride, acetylation of the 3-hydroxyl group in 3ξ-hydroxy-7β-(4-pyridylthio-acetylamino)-cepham-4α-carboxylic acid diphenylmethyl ester with acetic anhydride in the presence of pyridine and treatment of 3ξ-acetoxy-7β-(4-pyridylthio-acetylamino)-cepham-4α-carboxylic acid diphenylmethyl ester with triethylamine, followed by liberation of the acid by treatment with trifluoroacetic acid and anisole.

7β-Acetoacetyl-amino-3-cephem-4-carboxylic acid, thin layer chromatogram (silica gel); Rf = 0.3–0.4 (system: n-butanol/acetic acid/water, 75:7.5:21); ultraviolet absorption spectrum (in 0.1 M aqueous sodium bicarbonate solution): $\lambda_{max}$ at 238 mμ and 265 mμ; by oxidation of 3-methylene-7β-acetoacetyl-amino-cepham-4α-carboxylic acid diphenylmethyl ester with ozone, followed by treatment with dimethylsulphide, reduction of the keto group in 7β-acetoacetyl-amino-cepham-3-one-4α-carboxylic acid diphenylmethyl ester with sodium borohydride, acetylation of the 3-hydroxyl group in 3ξ-hydroxy-7β-acetoacetylamino-cepham-4α-carboxylic acid diphenylmethyl ester with acetic anhydride in the presence of pyridine and treatment of 3ξ-acetoxy-7β-acetoacetyl-amino-cepham-4α-carboxylic acid diphenylmethyl ester with triethylamine, followed by liberation of the acid by treatment with trifluoroacetic acid and anisole.

7β-Cyanoacetylamino-3-cephem-4-carboxylic acid, thin layer chromatogram (silica gel); Rf = 0.45–0.55 (system: n-butanol/pyridine/acetic acid/water, 38:24:8:30); ultraviolet absorption spectrum (in 0.1 M aqueous sodium bicarbonate solution): $\lambda_{max}$ at 254 mμ; infrared absorption spectrum (in mineral oil): characteristic bands at 4.32μ and 5.60μ; by oxidation of 3-methylene-7β-cyanoacetylamino-cepham-4α-carboxylic acid diphenylmethyl ester with ozone, followed by treatment with dimethylsulphide, reduction of the keto group in 7β-cyanoacetylamino-cepham-3-one-4α-carboxylic acid diphenylmethyl ester with sodium borohydride, acetylation of the 3-hydroxyl group in 3ξ-hydroxy-7β-cyanoacetylamino-cepham-4α-carboxylic acid diphenylmethyl ester with acetic anhydride in the presence of pyridine and treatment of 3ξ-acetoxy-7β-cyanoacetylamino-cepham-4α-carboxylic acid diphenylmethyl ester with triethylamine, followed by liberation of the acid by treatment with trifluoroacetic acid and anisole.

7β-(α-Cyanopropionyl-amino)-3-cephem-4-carboxylic acid, thin layer chromatogram (silica gel): Rf = 0.5–0.6 (system: n-butanol/pyridine/acetic acid/water, 38:24:8:30); ultraviolet absorption spectrum (in 0.1 M aqueous sodium bicarbonate solution): $\lambda_{max}$ at 255 mμ; infrared absorption spectrum (in mineral oil): characteristic bands at 4.44μ and 5.62μ; by oxidation of 3-methylene-7β-(α-cyanopropionylamino)-cepham-4α-carboxylic acid diphenylmethyl ester with ozone, followed by treatment with dimethylsulphide, reduction of the keto group in 7β-(α-cyanopropionyl-amino)-cepham-3-one-4α-carboxylic acid diphenylmethyl ester with sodium borohydride, acetylation of the 3-hydroxyl group in 3ξ-hydroxy-7β-(α-cyanopropionyl-amino)-cepham-4α-carboxylic acid diphenylmethyl ester with acetic anhydride in the presence of pyridine and treatment of 3ξ-acetoxy-7β-(α-cyanopropionyl-amino)-cepham-4α-carboxylic acid diphenylmethyl ester with triethylamine, followed by liberation of the acid by treatment with trifluoroacetic acid and anisole.

7β-(α-Cyano-α-phenylacetylamino)-3-cephem-4-carboxylic acid, thin layer chromatogram (silica gel): Rf = 0.3–0.4 (system: n-butanol/acetic acid/water, 75:7.5:21); ultraviolet absorption spectrum (in 0.1 M aqueous sodium bicarbonate solution): $\lambda_{max}$ at 260 mμ; infrared absorption spectrum (in mineral oil): characteristic bands at 4.42μ and 5.62μ; by oxidation of 3-methylene-7β-(α-cyano-α-phenylacetylamino)-cepham-4α-carboxylic acid diphenylmethyl ester with ozone, followed by treatment with dimethylsulphide, reduction of the keto group in 7β-(α-cyano-α-phenylacetylamino)-cepham-3-one-4α-diphenylmethyl ester with sodium borohydride, acetylation of the 3-hydroxyl group in 3ξ-hydroxy-7β-(α-cyano-α-phenylacetylamino)-cepham-4α-carboxylic acid diphenylmethyl ester with acetic anhydride in the presence of pyridine and treatment of 3ξ-acetoxy-7β-(α-cyano-α-phenylacetylamino)-cepham-4α-carboxylic acid diphenylmethyl ester with triethylamine, followed by liberation of the acid by treatment with trifluoroacetic acid and anisole.

7β-(D-α-Amino-α-4-hydroxyphenyl-acetylamino)-3-cephem-4-carboxylic acid in the form of the internal salt, melting point 220°–227° C (decomposition); ultraviolet absorption spectrum (in water): $\lambda_{inflexion} = 259$ mμ (ε = 5,450), $\lambda_{max} = 229$ mμ (ε = 2,250) and $\lambda_{min} = 218$ mμ (ε = 10,700); infrared absorption spectrum (in mineral oil): characteristic bands at 2.85μ (shoulder), 3.14μ, 5.66μ, 5.94μ, 6.21μ (shoulder), 6.27μ, 6.38μ and 6.59μ; thin layer chromatogram (silica gel; detection with ultraviolet light λ = 254 mμ, iodine vapour or ninhydrin and p,p'-bis-dimethylaminodiphenyl): Rf = 0.255 (system: n-butanol/acetic acid/water, 67:10:23), Rf = 0.61 (system: isopropanol/formic acid/water, 77:4:19) and Rf = 0.12 (system: ethyl acetate/n-butanol/pyridine/acetic acid/water, 42:21:21:6:10); by oxidation of 3-methylene-7β-(D-α-tert.-butoxycarbonylamino-α-4-hydroxyphenyl-acetylamino)-cepham-4α-carboxylic acid diphenylmethyl ester with ozone, followed by treatment with dimethylsulphide, reduction of the keto group in 7β-(D-α-tert.-butoxycarbonylamino-α-4-hydroxyphenyl-acetylamino)-cepham-3-one-4α-carboxylic acid diphenylmethyl ester with sodium borohydride, acetylation of the 3-hydroxyl group in 3ξ-hydroxy-7β-(D-α-tert.-butoxycarbonylamino-α-4-hydroxyphenyl-acetylamino)-cepham-4α-carboxylic acid diphenylmethyl ester with acetic anhydride in the presence of pyridine and treatment of 3ξ-acetoxy-7β-(D-α-tert.-butoxycarbonylamino-α-4-hydroxyphenyl-acetylamino)-cepham-4α-carboxylic acid diphenylmethyl ester with triethylamine, followed by liberation of the amino group and of the carboxyl group by treatment with trifluoroacetic acid and anisole.

7β-(D-α-Amino-α-2-thienyl-acetylamino)-3-cephem-4-carboxylic acid as a zwitter-ion, thin layer chromatogram (silica gel): Rf = 0.4–0.5 (system: ethyl acetate/methyl ethyl ketone/formic acid/water, 50:30:10:10); by oxidation of 3-methylene-7β-(D-α-tert.-butoxycarbonylamino-α-2-thienylacetylamino)-cepham-4α-carboxylic acid diphenylmethyl ester with ozone, followed by treatment with dimethylsulphide, reduction of the keto group in 7β-(D-α-tert.-butoxycarbonylamino-α-2-thienyl-acetylamino)-cepham-3-one-4α-carboxylic acid diphenylmethyl ester with sodium borohydride, acetylation of the 3-hydroxyl group in 3ξ-hydroxy-7β-(D-α-tert.-butoxycarbonylamino-α-2-thienyl-acetylamino)-cepham-4α-carboxylic acid diphenylmethyl ester with acetic anhydride in the presence of pyridine and treatment of 3ξ-acetoxy-7β-(D-α-tert.-butoxycarbonylamino-α-2-thienyl-acetylamino)-cepham-4α-carboxylic acid diphenylmethyl ester with triethylamine, followed by liberation of the amino group and of the carboxyl group by treatment with trifluoroacetic acid and anisole.

7β-(D-α-Amino-α-4-isothiazolyl-acetylamino)-3-cephem-4-carboxylic acid in the form of the internal salt, thin layer chromatogram (silica gel): Rf = 0.32 (system: n-butanol/acetic acid/water, 75:7.5:21) and Rf = 0.62 (system: isopropanol/formic acid/water, 77:4:19); ultraviolet absorption spectrum (in ethanol): $\lambda_{max} = 248$ mμ (ε = 6,100) and $\lambda_{min} = 230$ mμ (ε = 4,100); infrared absorption spectrum (in mineral oil): characteristic bands at 2.85μ, 3.10μ, 3.25μ, 5.62μ, 5.92μ, 6.10μ and 8.02μ; by oxidation of 3-methylene-7β-(D-α-tert.-butoxycarbonylamino-α-4-isothiazolyl-acetylamino)-cepham-4α-carboxylic acid diphenylmethyl ester with ozone, followed by treatment with dimethylsulphide, reduction of the keto group in 7β-(D-α-tert.-butoxycarbonylamino-α-4-isothiazolyl-acetylamino)-cepham-3-one-4α-carboxylic acid diphenylmethyl ester with sodium borohydride, acetylation of the 3-hydroxyl group in 3ξ-hydroxy-7β-(D-α-tert.-butoxycarbonylamino-α-4-isothiazolyl-acetylamino)-cepham-4α-carboxylic acid diphenylmethyl ester with acetic anhydride in the presence of pyridine and treatment of 3ξ-acetoxy-7β-(D-α-tert.-butoxycarbonylamino-α-4-isothiazolyl-acetylamino)-cepham-4α-carboxylic acid diphenylmethyl ester with trimethylamine, followed by liberation of the amino group and of the carboxyl group by treatment with trifluoroacetic acid and anisole.

7β-Phenylacetylamino-3-cephem-4-carboxylic acid diphenylmethyl ester-1-oxide, melting point 198° – 202° (uncorrected); $[\alpha]_D^{20} = +112° \pm 1°$ (c = 0.667 in chloroform); ultraviolet absorption spectrum (95% strength aqueous ethanol): $\lambda_{max} = 264$ mμ (ε = 6,860) and $\lambda_{min} = 240$ (ε = 3,930); by oxidation of 3-methylene-7β-phenylacetylamino-cepham-4-α-carboxylic acid diphenylmethyl ester with ozone, followed by treatment with dimethylsulphide and elimination of the 7β-phenylacetylamino-cepham-3-one-4α-carboxylic acid diphenylmethyl ester-1-oxide obtained as a by-product, reduction of the keto group with sodium borohydride, acetylation of the 3-hydroxyl group in 3ξ-hydroxy-7β-phenylacetylamino-cepham-4α-carboxylic acid diphenylmethyl ester-1-oxide with acetic anhydride in the presence of pyridine and treatment of 3ξ-acetoxy-7β-phenylacetylamino-cepham-4α-carboxylic acid diphenylmethyl ester-1-oxide with triethylamine.

7β-(D-α-Phenyl-glycylamino)-3-cephem-4-carboxylic acid, yellowish amorphous powder, thin layer chromatogram (silica gel: developing with iodine vapour): Rf = 0.29 (system: n-butanol/pyridine/acetic acid/water, 40:24:6:30); ultraviolet absorption spectrum (in water): $\lambda_{max} = 250$ mμ ($\epsilon = 4,300$); by acetylation of the 3-hydroxyl group in 3ξ-hydroxy-7β-(D-α-tert.-butoxycarbonylamino-α-phenylacetylamino)-cepham-4α-carboxylic acid diphenylmethyl ester with acetic anhydride in the presence of pyridine and treatment of 3ξ-acetoxy-7β-(D-α-tert.-butoxycarbonylamino-α-phenylacetylamino)-cepham-4α-carboxylic acid diphenylmethyl ester with triethylamine, followed by liberation of the acid by treatment with trifluoroacetic acid and anisole.

We claim:

1. A 7β-amino-cepham-3-ol-4-carboxylic acid compound of the formula

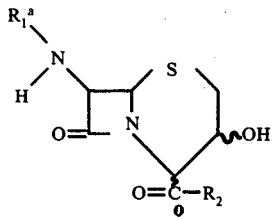

(I)

wherein $R_1{}^a$ represents hydrogen, a group of the formula

(A₁)

in which $R'$ represents cycloalkyl having 5–7 ring carbon atoms and being substituted in the 1-position by amino, protected amino, sulphoamino or sulphoamino in salt-form, phenyl, or phenyl substituted by hydroxy, protected hydroxyl, lower alkoxy, or halogen, or $R_1{}^a$ represents a group of the formula

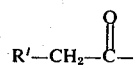

(A₂)

in which $R'$ represents phenyl, hydroxy-phenyl, protected hydroxyphenyl, halogeno-phenyl, hydroxy-halogeno-phenyl, protected hydroxy-halogeno-phenyl, amino-lower alkyl-phenyl, protected amino-lower alkyl-phenyl, phenyloxyphenyl, phenyloxy, hydroxy-phenyloxy, protected hydroxy-phenyloxy, halogeno-phenyloxy, or phenylthio, or $R_1{}^a$ represents a group of the formula

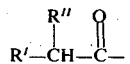

(A₃)

in which $R'$ represents phenyl, hydroxy-phenyl, protected hydroxy-phenyl, halogeno-phenyl, hydroxy-halogeno-phenyl, protected hydroxy-halogeno-phenyl, or 1,4-cyclohexadienyl, $R''$ represents amino, protected amino, arylthioamino, tritylthioamino, 2-propylideneamino which contains lower alkoxycarbonyl or lower alkanoyl as substituent in 1-position, guanidino-carbonylamino, sulphoamino, sulphoamino in salt-form, azido, carboxyl, carboxyl in salt-form, carboxyl protected in esterified form, cyano, sulpho, hydroxy, protected hydroxy, O-lower alkyl-phosphono, O,O'-di-lower alkylphosphone, halogeno, aminomethyl, protected aminomethyl, and $R_2$ is hydroxyl, lower alkoxy, lower alkoxy substituted in 2-position by halogen or in 1-position by phenyl, 4-methoxyphenyl, 4-nitrophenyl or lower alkanoyloxy, tri-lower alkyl-silyloxy, amino, lower alkylamino, di-lower alkylamino, lower alkyleneamino, oxa-lower alkyleneamino, hydroxylamino, hydrazino, 2-lower alkylhydrazino or 2,2-di-lower alkylhydrazino, and 3-O-esters thereof with a hydrogen halide acid, a lower alkanesulphonic acid, phenylsulphonic acid, 4-methylphenylsulfonic acid, a lower alkanecarboxylic acid, or benzoic acid, and salts of such compounds.

2. A 7β-amino-cepham-3-ol-4-carboxylic acid compound of the formula

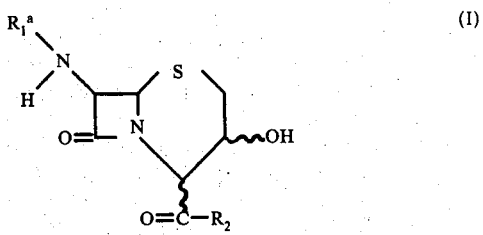

(I)

wherein $R_1{}^a$ represents hydrogen, a group of the formula

 (A₁)

in which $R'$ represents cycloalkyl having 5–7 ring carbon atoms and being substituted in the 1-position by amino, lower alkoxycarbonylamino, 2-halogeno-lower alkoxycarbonylamino, sulphoamino or sulphoamino in salt-form, phenyl, or phenyl substituted by hydroxyl, lower alkoxy, lower-alkoxycarbonyloxy, 2-halogeno-lower alkoxycarbonyloxy or halogen, or $R_1{}^a$ represents a group of the formula

 (A₂)

in which $R'$ represents phenyl, hydroxy-phenyl, lower alkoxycarbonyloxy-phenyl, 2-halogeno-lower alkoxycarbonyloxyphenyl, halogenophenyl, hydroxy-halogeno-phenyl, lower alkoxycarbonyloxy-halogenophenyl, 2-halogeno-lower alkoxycarbonyloxyhalogenophenyl, amino-lower alkyl-phenyl, lower alkoxycarbonylamino-lower alkyl-phenyl, 2-halogeno-lower alkoxycarbonylamino-lower alkylphenyl, phenyloxyphenyl, phenyloxy, hydroxy-phenyloxy, lower alkoxycarbonyloxy-phenyloxy, 2-halogeno-lower alkoxycarbonyloxy-phenyloxy, halogeno-phenyloxy, or phenylthio, or $R_1{}^a$ represents a group of the formula

 (A₃)

in which $R'$ represents phenyl, hydroxy-phenyl, lower alkoxycarbonyloxy-phenyl, 2-halogeno-lower alkoxycarbonyloxyphenyl, halogeno-phenyl, hydroxy-halogeno-phenyl, lower alkoxycarbonyloxy-halogenophenyl, 2-halogeno-lower alkoxycarbonyloxy-halogeno-phenyl, or 1,4-cyclohexadienyl, and $R''$ represents amino, lower alkoxycarbonylamino, 2-halogeno-lower alkoxycarbonylamino, tritylamino, arylthioamino, tritylthioamino, 2-propylideneamino which contains lower alkoxycarbonyl or lower alkanoyl as substituent in 1-position, guanidinocarbonylamino, sulphoamino, sulphoamino in salt-form, axido, carboxyl, carboxyl in salt-form, carboxyl in esterified form, cyano, sulpho, hydroxy, lower alkoxycarbonyloxy, 2-halogeno-lower alkylcarbonyloxy, O-lower alkyl-phosphono, O,O'-di-lower alkyl-phosphone, halogeno, aminomethyl, lower alkoxycarbonylaminomethyl or 2-halogeno-lower alkyloxycarbonyl-aminomethyl, and $R_2$ is hydroxyl, lower alkoxy, lowr alkoxy substituted in 2-position by halogen or in 1-position by phenyl, 4-methoxyphenyl, 4-nitrophenyl or lower alkanoyloxy, tri-lower alkylsilyloxy, amino, lower alkylamino, di-lower alkylamino, lower alkyleneamino, oxa-lower alkyleneamino, hydroxylamino, hydrazino, 2-lower alkylhydrazino or 2,2-di-lower alkylhydrazino, and 3-O-esters thereof with a hydrogen halide acid, a lower alkanesulphonic acid, phenylsulphonic acid, 4-methylphenylsulfonic acid, a lower alkanecarboxylic acid, or benzoic acid, and salts of such compounds.

3. A 7β-amino-cepham-3-ol-4-carboxylic acid compound of the formula I according to claim 2, wherein $R_1{}^a$ represents a group of the formula

 (A₁)

in which $R'$ represents phenyl, hydroxy-phenyl, lower alkoxycarbonyloxy-phenyl, 2-halogeno-lower alkoxycarbonyloxyphenyl, halogenophenyl, hydroxy-halogeno-phenyl, lower alkoxycarbonyloxy-halogenophenyl, 2-halogeno-lower alkoxycarbonyloxy-halogeno-phenyl, amino-lower alkyl-phenyl, lower alkoxycarbonylamino-lower alkyl-phenyl, 2-halogeno-lower alkoxycarbonylamino-lower alkylphenyl, phenyloxyphenyl, phenyloxy, hydroxyphenyloxy, lower alkoxycarbonyloxy-phenyloxy, 2-halogeno-lower alkoxycarbonyloxy-phenyloxy, halogeno-phenyloxy, or phenylthio, or $R_1{}^a$ represents a group of the formula

 (A₂)

in which $R'$ represents phenyl, hydroxy-phenyl, lower alkoxycarbonyloxy-phenyl, 2-halogeno-lower alkoxycarbonyloxyphenyl, halogeno-phenyl, hydroxy-halogeno-phenyl, lower alkoxycarbonyloxy-halogenophenyl, 2-halogeno-lower alkoxycarbonyloxy-halogeno-phenyl, or 1,4-cyclohexadienyl, and $R''$ represents amino, lower alkoxycarbonylamino, 2-halogeno-lower alkoxycarbonylamino, sulphoamino, sulphoamino in salt-form, carboxyl, carboxyl in salt-form, carboxyl in esterified form, sulpho, hydroxy, lower alkoxy-carbonyloxy, 2-halogeno-lower alkylcarbonyloxy, O-lower alkyl-phosphono, or O,O'-di-lower alkylphosphone, and $R_2$ is hydroxyl, lower alkoxy, 2-halogeno-lower alkoxy, diphenylmethoxy, 4-methoxybenzyloxy, 4-nitrobenzyloxy and 3-O-esters thereof with a lower alkanecarboxylic acid, and salts of such compounds.

4. A 7β-amino-cepham-3-ol-4-carboxylic acid compound of the formula I according to claim 2, wherein $R_1{}^a$ represnts a group of the formula

 (A₁)

in which $R'$ represents phenyl, hydroxy-phenyl, lower alkoxycarbonyloxy-phenyl, 2-halogeno-lower alkoxycarbonyloxyphenyl, phenyloxy, or $R_1{}^a$ represents a group of the formula

 (A₂)

in which $R'$ represents phenyl, hydroxy-phenyl, lower alkoxycarbonyloxy-phenyl, 2-halogeno-lower alkoxycarbonyloxyphenyl, or 1,4-cyclohexadienyl, and $R''$ represents amino, lower alkoxycarbonylamino, 2-halogen-lower alkoxycarbonylamino, hydroxy, lower alkoxy-carbonyloxy, or 2-halogeno-lower alkylcarbonyloxy, and $R_2$ is hydroxy, lower alkoxy, 2-halogenolower alkoxy, diphenylmethoxy, 4-methoxybenzyloxy, 4-nitrobenzyloxy, and 3-O-esters thereof with a lower alkanecarboxylic acid, or acid, and salts of such compounds.

5. A compound as claimed in claim 2 and being a member selected from the group consisting of 7β-(α-R'-α-R''-acetylamino)-cepham-3-ol-4-carboxylic acids and 3-O-acetyl compounds thereof and the diphenylmethyl esters thereof, in which R' is phenyl and R'' represents hydrogen, amino, lower akoxycarbonylamino or 2-halogeno-lower alkoxycarbonylamino and salts of such compounds.

6. A compound as claimed in claim 2 and being 3ξ-hydroxy-7β-phenyl-acetylamino-cepham-4α-carboxylic acid diphenylmethyl ester.

7. A compound as claimed in claim 2 and being 3ξ-acetyloxy-7β-phenyl-acetylamino-cepham-4α-carboxylic acid diphenylmethyl ester.

* * * * *